(12) United States Patent
Phung et al.

(10) Patent No.: US 11,775,613 B2
(45) Date of Patent: *Oct. 3, 2023

(54) METHODS OF SAFELY EXPANDING PROSTHETIC HEART VALVES

(71) Applicant: Edwards Lifesciences Corporation, Irvine, CA (US)

(72) Inventors: Andrew Phung, Brea, CA (US); August R. Yambao, Temecula, CA (US); Faisal Kalam, Corona, CA (US); William C. Brunnett, Mission Viejo, CA (US); Rafael Pintor, Mission Viejo, CA (US); Michael J. Scott, San Diego, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 61 days.

This patent is subject to a terminal disclaimer.

(21) Appl. No.: 17/644,323

(22) Filed: Dec. 14, 2021

(65) Prior Publication Data

US 2022/0172001 A1 Jun. 2, 2022

Related U.S. Application Data

(60) Continuation of application No. 16/779,429, filed on Jan. 31, 2020, now Pat. No. 11,197,757, which is a
(Continued)

(51) Int. Cl.
*A61F 2/24* (2006.01)
*G06F 18/214* (2023.01)
(Continued)

(52) U.S. Cl.
CPC ........ *G06F 18/2148* (2023.01); *A61F 2/2412* (2013.01); *A61F 2/2418* (2013.01);
(Continued)

(58) Field of Classification Search
CPC ........ A61M 2025/006; A61M 25/0606; A61M 25/0625; A61M 2039/0288;
(Continued)

(56) References Cited

U.S. PATENT DOCUMENTS 30,912 A 12/1860 Hancock
3,143,742 A 8/1964 Cromie
(Continued)

FOREIGN PATENT DOCUMENTS

EP 0084395 A1 7/1983
EP 0096721 A1 12/1983
(Continued)

OTHER PUBLICATIONS

Krakow, "3F Therapeutics, Inc. Announces the First Clinical Implantation of the 3F Enable Aortic Heart Valve, a Patented, Sutureless Implantation, Replacement Heart Valve Intended to Save Valuable Surgery Time and Reduce Time Related Complications . . . " Healthcare Sales & Marketing Network News Feed, Jan. 18, 2005, pp. 1-2.
(Continued)

*Primary Examiner* — Erich G Herbermann
(74) *Attorney, Agent, or Firm* — Guy Cumberbatch

(57) ABSTRACT

Methods of quickly and easily implanting a quick-connect heart valve prosthesis during a surgical procedure are provided. The heart valve may include a substantially non-expandable, non-compressible prosthetic valve and a plastically-expandable frame, thereby enabling attachment to the annulus without sutures. A system and method for deployment includes an integrated handle shaft and balloon catheter. A safety member disposed between the balloon catheter and handle shaft prevents premature catheter advancement
(Continued)

prior to heart valve placement at the annulus, and also may prevent premature balloon inflation prior to full catheter advancement.

20 Claims, 17 Drawing Sheets

Related U.S. Application Data division of application No. 15/368,335, filed on Dec. 2, 2016, now Pat. No. 10,548,728, which is a continuation of application No. 14/847,190, filed on Sep. 8, 2015, now Pat. No. 9,968,450, which is a division of application No. 13/797,572, filed on Mar. 12, 2013, now Pat. No. 9,125,741, which is a continuation-in-part of application No. 13/167,639, filed on Jun. 23, 2011, now Pat. No. 8,641,757.

(60) Provisional application No. 61/381,931, filed on Sep. 10, 2010.

(51) Int. Cl.
*G06F 40/169* (2020.01)
*G06V 10/25* (2022.01)
*G06N 3/08* (2023.01)

(52) U.S. Cl.
CPC .......... *A61F 2/2433* (2013.01); *A61F 2/2466* (2013.01); *G06F 40/169* (2020.01); *G06N 3/08* (2013.01); *G06V 10/25* (2022.01); *A61F 2220/0008* (2013.01); *A61F 2220/0016* (2013.01)

(58) Field of Classification Search
CPC . A61M 2039/1066; A61M 39/20; A61F 2/95; A61F 2/2427; A61F 2/243; A61F 2/2433; A61F 2/2436; A61F 2/2439; A61F 2002/9517; A61F 2/2412; A61F 2/2418; A61F 2220/0008; A61F 2220/0016; A61F 2/24; A61F 2/2421; A61F 2/2424
See application file for complete search history.

(56) References Cited

U.S. PATENT DOCUMENTS

| | | |
|---|---|---|
| 3,320,972 A | 5/1967 | High et al. |
| 3,371,352 A | 3/1968 | Siposs et al. |
| 3,409,013 A | 11/1968 | Berry |
| 3,546,710 A | 12/1970 | Shumakov et al. |
| 3,574,865 A | 4/1971 | Hamaker |
| 3,628,535 A | 12/1971 | Ostrowsky et al. |
| 3,657,744 A | 4/1972 | Ersek |
| 3,686,740 A | 8/1972 | Shiley |
| 3,755,823 A | 9/1973 | Hancock |
| 3,839,741 A | 10/1974 | Haller |
| 4,035,849 A | 7/1977 | Angell et al. |
| 4,078,468 A | 3/1978 | Civitello |
| 4,079,468 A | 3/1978 | Liotta et al. |
| 4,084,268 A | 4/1978 | Ionescu et al. |
| 4,106,129 A | 8/1978 | Carpentier et al. |
| 4,172,295 A | 10/1979 | Batten |
| 4,211,325 A | 7/1980 | Wright |
| 4,217,665 A | 8/1980 | Bex et al. |
| 4,218,782 A | 8/1980 | Rygg |
| 4,259,753 A | 4/1981 | Liotta et al. |
| 4,340,091 A | 7/1982 | Skelton et al. |
| 4,343,048 A | 8/1982 | Ross et al. |
| 4,364,126 A | 12/1982 | Rosen et al. |
| 4,388,735 A | 6/1983 | Ionescu et al. |
| 4,441,216 A | 4/1984 | Ionescu et al. |
| 4,451,936 A | 6/1984 | Carpentier et al. |
| 4,470,157 A | 9/1984 | Love |
| 4,490,859 A | 1/1985 | Black et al. |
| 4,496,348 A | 1/1985 | Genese et al. |
| 4,501,030 A | 2/1985 | Lane |
| 4,506,394 A | 3/1985 | Bedard |
| 4,535,483 A | 8/1985 | Klawitter et al. |
| 4,605,407 A | 8/1986 | Black et al. |
| 4,626,255 A | 12/1986 | Reichart et al. |
| 4,629,459 A | 12/1986 | Ionescu et al. |
| 4,680,031 A | 7/1987 | Alonso |
| 4,687,483 A | 8/1987 | Fisher et al. |
| 4,702,250 A | 10/1987 | Ovil et al. |
| 4,705,516 A | 11/1987 | Barone et al. |
| 4,725,274 A | 2/1988 | Lane et al. |
| 4,731,074 A | 3/1988 | Rousseau et al. |
| 4,778,461 A | 10/1988 | Pietsch et al. |
| 4,790,843 A | 12/1988 | Carpentier et al. |
| 4,851,000 A | 7/1989 | Gupta |
| 4,865,600 A | 9/1989 | Carpentier et al. |
| 4,888,009 A | 12/1989 | Lederman et al. |
| 4,914,097 A | 4/1990 | Oda et al. |
| 4,960,424 A | 10/1990 | Grooters |
| 4,993,428 A | 2/1991 | Arms |
| 5,010,892 A | 4/1991 | Colvin et al. |
| 5,032,128 A | 7/1991 | Alonso |
| 5,037,434 A | 8/1991 | Lane |
| 5,147,391 A | 9/1992 | Lane |
| 5,163,953 A | 11/1992 | Vince |
| 5,163,955 A | 11/1992 | Love et al. |
| 5,258,023 A | 11/1993 | Reger |
| 5,290,300 A | 3/1994 | Cosgrove et al. |
| 5,316,016 A | 5/1994 | Adams et al. |
| 5,326,370 A | 7/1994 | Love et al. |
| 5,326,371 A | 7/1994 | Love et al. |
| 5,332,402 A | 7/1994 | Teitelbaum |
| 5,360,444 A | 11/1994 | Kusuhara |
| 5,370,685 A | 12/1994 | Stevens |
| 5,376,112 A | 12/1994 | Duran |
| 5,396,887 A | 3/1995 | Imran |
| 5,397,351 A | 3/1995 | Pavcnik et al. |
| 5,411,522 A | 5/1995 | Trott |
| 5,411,552 A | 5/1995 | Andersen et al. |
| 5,423,887 A | 6/1995 | Love et al. |
| 5,425,741 A | 6/1995 | Lemp et al. |
| 5,431,676 A | 7/1995 | Dubrul et al. |
| 5,449,384 A | 9/1995 | Johnson |
| 5,449,385 A | 9/1995 | Religa et al. |
| 5,469,868 A | 11/1995 | Reger |
| 5,476,510 A | 12/1995 | Eberhardt et al. |
| 5,488,789 A | 2/1996 | Religa et al. |
| 5,489,297 A | 2/1996 | Duran |
| 5,489,298 A | 2/1996 | Love et al. |
| 5,500,016 A | 3/1996 | Fisher |
| 5,522,884 A | 6/1996 | Wright |
| 5,531,785 A | 7/1996 | Love et al. |
| 5,533,515 A | 7/1996 | Coller et al. |
| 5,549,665 A | 8/1996 | Vesely et al. |
| 5,562,729 A | 10/1996 | Purdy et al. |
| 5,571,215 A | 11/1996 | Sterman et al. |
| 5,573,007 A | 11/1996 | Bobo, Sr. |
| 5,578,076 A | 11/1996 | Krueger et al. |
| 5,584,803 A | 12/1996 | Stevens et al. |
| 5,618,307 A | 4/1997 | Donlon et al. |
| 5,626,607 A | 5/1997 | Malecki et al. |
| 5,628,789 A | 5/1997 | Vanney et al. |
| 5,693,090 A | 12/1997 | Unsworth et al. |
| 5,695,503 A | 12/1997 | Krueger et al. |
| 5,713,952 A | 2/1998 | Vanney et al. |
| 5,716,370 A | 2/1998 | Williamson, IV et al. |
| 5,728,064 A | 3/1998 | Burns et al. |
| 5,728,151 A | 3/1998 | Garrison et al. |
| 5,735,894 A | 4/1998 | Krueger et al. |
| 5,752,522 A | 5/1998 | Murphy |
| 5,755,782 A | 5/1998 | Love et al. |
| 5,766,240 A | 6/1998 | Johnson |
| 5,776,187 A | 7/1998 | Krueger et al. |
| 5,776,188 A | 7/1998 | Shepherd et al. |
| 5,800,527 A | 9/1998 | Jansen et al. |
| 5,814,097 A | 9/1998 | Sterman et al. |

(56) References Cited

U.S. PATENT DOCUMENTS

| | | |
|---|---|---|
| 5,814,098 A | 9/1998 | Hinnenkamp et al. |
| 5,824,064 A | 10/1998 | Taheri |
| 5,824,068 A | 10/1998 | Bugge |
| 5,840,081 A | 11/1998 | Andersen et al. |
| 5,848,969 A | 12/1998 | Panescu et al. |
| 5,855,563 A | 1/1999 | Kaplan et al. |
| 5,855,601 A | 1/1999 | Bessler et al. |
| 5,865,801 A | 2/1999 | Houser |
| 5,891,160 A | 4/1999 | Williamson, IV et al. |
| 5,895,420 A | 4/1999 | Mirsch, II et al. |
| 5,902,308 A | 5/1999 | Murphy |
| 5,908,450 A | 6/1999 | Gross et al. |
| 5,919,147 A | 7/1999 | Jain |
| 5,921,934 A | 7/1999 | Teo |
| 5,921,935 A | 7/1999 | Hickey |
| 5,924,984 A | 7/1999 | Rao |
| 5,928,281 A | 7/1999 | Huynh et al. |
| 5,957,949 A | 9/1999 | Leonhardt et al. |
| 5,972,004 A | 10/1999 | Williamson, IV et al. |
| 5,984,959 A | 11/1999 | Robertson et al. |
| 5,984,973 A | 11/1999 | Girard et al. |
| 6,010,531 A | 1/2000 | Donlon et al. |
| 6,042,607 A | 3/2000 | Williamson, IV et al. |
| 6,059,827 A | 5/2000 | Fenton, Jr. |
| 6,066,160 A | 5/2000 | Colvin et al. |
| 6,074,418 A | 6/2000 | Buchanan et al. |
| 6,081,737 A | 6/2000 | Shah |
| 6,083,179 A | 7/2000 | Oredsson |
| 6,099,475 A | 8/2000 | Seward et al. |
| 6,106,550 A | 8/2000 | Magovern et al. |
| 6,110,200 A | 8/2000 | Hinnenkamp |
| 6,117,091 A | 9/2000 | Young et al. |
| 6,126,007 A | 10/2000 | Kari et al. |
| 6,162,233 A | 12/2000 | Williamson, IV et al. |
| 6,168,614 B1 | 1/2001 | Andersen et al. |
| 6,176,877 B1 | 1/2001 | Buchanan et al. |
| 6,197,054 B1 | 3/2001 | Hamblin, Jr. et al. |
| 6,200,306 B1 | 3/2001 | Klostermeyer et al. |
| 6,217,611 B1 | 4/2001 | Klostermeyer |
| 6,231,561 B1 | 5/2001 | Frazier et al. |
| 6,241,765 B1 | 6/2001 | Griffin et al. |
| 6,245,102 B1 | 6/2001 | Jayaraman |
| 6,264,611 B1 | 7/2001 | Ishikawa et al. |
| 6,264,691 B1 | 7/2001 | Gabbay |
| 6,283,127 B1 | 9/2001 | Sterman et al. |
| 6,287,339 B1 | 9/2001 | Vazquez et al. |
| 6,312,447 B1 | 11/2001 | Grimes |
| 6,312,465 B1 | 11/2001 | Griffin et al. |
| 6,322,526 B1 | 11/2001 | Rosenman et al. |
| 6,328,727 B1 | 12/2001 | Frazier et al. |
| 6,350,282 B1 | 2/2002 | Eberhardt |
| 6,358,240 B1 | 3/2002 | Campbell et al. |
| 6,371,983 B1 | 4/2002 | Lane |
| 6,402,780 B2 | 6/2002 | Williamson, IV et al. |
| 6,425,916 B1 | 7/2002 | Garrison et al. |
| 6,454,799 B1 | 9/2002 | Schreck |
| 6,458,100 B2 | 10/2002 | Roue et al. |
| 6,458,153 B1 | 10/2002 | Bailey et al. |
| 6,468,305 B1 | 10/2002 | Otte |
| 6,491,624 B1 | 12/2002 | Lotfi |
| 6,530,952 B2 | 3/2003 | Vesely |
| 6,558,429 B2 | 5/2003 | Taylor |
| 6,569,196 B1 | 5/2003 | Vesely |
| 6,582,462 B1 | 6/2003 | Andersen et al. |
| 6,585,766 B1 | 7/2003 | Huynh et al. |
| 6,682,559 B2 | 1/2004 | Myers et al. |
| 6,685,739 B2 | 2/2004 | DiMatteo et al. |
| 6,702,825 B2 | 3/2004 | Frazier et al. |
| 6,712,804 B2 | 3/2004 | Roue et al. |
| 6,719,789 B2 | 4/2004 | Cox |
| 6,730,118 B2 | 5/2004 | Spenser et al. |
| 6,733,525 B2 | 5/2004 | Yang et al. |
| 6,746,472 B2 | 6/2004 | Frazier et al. |
| 6,764,508 B1 | 7/2004 | Roehe et al. |
| 6,767,362 B2 | 7/2004 | Schreck |
| 6,773,457 B2 | 8/2004 | Ivancev et al. |
| 6,786,925 B1 | 9/2004 | Schoon et al. |
| 6,790,229 B1 | 9/2004 | Berreklouw |
| 6,790,230 B2 | 9/2004 | Beyersdorf et al. |
| 6,805,711 B2 | 10/2004 | Quijano et al. |
| 6,846,325 B2 | 1/2005 | Liddicoat |
| 6,893,459 B1 | 5/2005 | Macoviak |
| 6,893,460 B2 | 5/2005 | Spenser et al. |
| 6,936,067 B2 | 8/2005 | Buchanan |
| 6,939,365 B1 | 9/2005 | Fogarty et al. |
| 6,964,682 B2 | 11/2005 | Nguyen-Thien-Nhon et al. |
| 6,974,476 B2 | 12/2005 | McGuckin, Jr. et al. |
| 6,978,176 B2 | 12/2005 | Lattouf |
| 7,011,681 B2 | 3/2006 | Vesely |
| 7,018,404 B2 | 3/2006 | Holmberg et al. |
| 7,025,780 B2 | 4/2006 | Gabbay |
| 7,037,333 B2 | 5/2006 | Myers et al. |
| 7,070,616 B2 | 7/2006 | Majercak et al. |
| 7,081,131 B2 | 7/2006 | Thornton |
| 7,097,659 B2 | 8/2006 | Woolfson et al. |
| 7,101,396 B2 | 9/2006 | Artof et al. |
| 7,147,663 B1 | 12/2006 | Berg et al. |
| 7,153,324 B2 | 12/2006 | Case et al. |
| 7,160,320 B2 | 1/2007 | Duran |
| 7,172,625 B2 | 2/2007 | Shu et al. |
| 7,186,265 B2 | 3/2007 | Sharkawy et al. |
| 7,195,641 B2 | 3/2007 | Palmaz et al. |
| 7,201,771 B2 | 4/2007 | Lane |
| 7,201,772 B2 | 4/2007 | Schwammenthal et al. |
| 7,238,200 B2 | 7/2007 | Lee et al. |
| 7,252,682 B2 | 8/2007 | Seguin |
| 7,261,732 B2 | 8/2007 | Justino |
| 7,300,463 B2 | 11/2007 | Liddicoat |
| 7,311,730 B2 | 12/2007 | Gabbay |
| RE40,377 E | 6/2008 | Williamson, IV et al. |
| 7,393,360 B2 | 7/2008 | Spenser et al. |
| 7,422,603 B2 | 9/2008 | Lane |
| 7,429,269 B2 | 9/2008 | Schwammenthal et al. |
| 7,442,204 B2 | 10/2008 | Schwammenthal et al. |
| 7,445,630 B2 | 11/2008 | Lashinski et al. |
| 7,445,631 B2 | 11/2008 | Salahieh et al. |
| 7,468,073 B2 | 12/2008 | Johnson et al. |
| 7,470,285 B2 | 12/2008 | Nugent et al. |
| 7,510,575 B2 | 3/2009 | Spenser et al. |
| 7,513,909 B2 | 4/2009 | Lane et al. |
| 7,524,330 B2 | 4/2009 | Berreklouw |
| 7,534,261 B2 | 5/2009 | Friedman |
| 7,556,647 B2 | 7/2009 | Drews et al. |
| 7,569,072 B2 | 8/2009 | Berg et al. |
| 7,578,843 B2 | 8/2009 | Shu |
| 7,585,321 B2 | 9/2009 | Cribier |
| 7,591,848 B2 | 9/2009 | Allen |
| 7,597,711 B2 | 10/2009 | Drews et al. |
| 7,611,535 B2 | 11/2009 | Woolfson et al. |
| 7,618,446 B2 | 11/2009 | Andersen et al. |
| 7,618,447 B2 | 11/2009 | Case et al. |
| 7,622,276 B2 | 11/2009 | Cunanan et al. |
| 7,625,403 B2 | 12/2009 | Krivoruchko |
| 7,641,687 B2 | 1/2010 | Chinn et al. |
| 7,658,763 B2 | 2/2010 | Stobie |
| 7,682,390 B2 | 3/2010 | Seguin |
| 7,704,277 B2 | 4/2010 | Zakay et al. |
| 7,708,775 B2 | 5/2010 | Rowe et al. |
| 7,727,276 B2 | 6/2010 | Machiraju |
| 7,740,655 B2 | 6/2010 | Birdsall |
| 7,799,069 B2 | 9/2010 | Bailey et al. |
| 7,822,414 B2 | 10/2010 | Bender et al. |
| 7,862,610 B2 | 1/2011 | Quintessenza |
| 7,887,583 B2 | 2/2011 | Macoviak |
| 7,896,913 B2 | 3/2011 | Damm et al. |
| 7,947,072 B2 | 5/2011 | Yang et al. |
| 7,951,197 B2 | 5/2011 | Lane et al. |
| 7,967,857 B2 | 6/2011 | Lane |
| 7,972,377 B2 | 7/2011 | Lane |
| 7,989,157 B2 | 8/2011 | Cunanan et al. |
| 7,998,151 B2 | 8/2011 | St. Goar et al. |
| 8,062,355 B2 | 11/2011 | Figulla et al. |
| 8,167,932 B2 | 5/2012 | Bourang |
| 8,246,675 B2 | 8/2012 | Zegdi |

(56) References Cited

U.S. PATENT DOCUMENTS

| | | |
|---|---|---|
| 8,246,678 B2 | 8/2012 | Salahieh et al. |
| 8,308,798 B2 | 11/2012 | Pintor et al. |
| 8,323,337 B2 | 12/2012 | Gurskis et al. |
| 8,348,998 B2 | 1/2013 | Pintor et al. |
| 8,353,953 B2 | 1/2013 | Giannetti et al. |
| 8,500,798 B2 | 8/2013 | Rowe et al. |
| 8,821,569 B2 | 9/2014 | Gurskis et al. |
| 2001/0007956 A1 | 7/2001 | Letac et al. |
| 2001/0021872 A1 | 9/2001 | Bailey et al. |
| 2001/0041914 A1 | 11/2001 | Frazier et al. |
| 2002/0026238 A1 | 2/2002 | Lane et al. |
| 2002/0032481 A1 | 3/2002 | Gabbay |
| 2002/0058995 A1 | 5/2002 | Stevens |
| 2002/0077698 A1 | 6/2002 | Peredo |
| 2002/0123802 A1 | 9/2002 | Snyders |
| 2002/0138138 A1 | 9/2002 | Yang |
| 2002/0151970 A1 | 10/2002 | Garrison et al. |
| 2002/0188348 A1 | 12/2002 | DiMatteo et al. |
| 2002/0198594 A1 | 12/2002 | Schreck |
| 2003/0014104 A1 | 1/2003 | Cribier |
| 2003/0023300 A1 | 1/2003 | Bailey et al. |
| 2003/0023303 A1 | 1/2003 | Palmaz et al. |
| 2003/0040792 A1 | 2/2003 | Gabbay |
| 2003/0055495 A1 | 3/2003 | Pease et al. |
| 2003/0105519 A1 | 6/2003 | Fasol et al. |
| 2003/0109924 A1 | 6/2003 | Cribier |
| 2003/0114913 A1 | 6/2003 | Spenser et al. |
| 2003/0130729 A1 | 7/2003 | Paniagua et al. |
| 2003/0149478 A1 | 8/2003 | Figulla et al. |
| 2003/0167089 A1 | 9/2003 | Lane |
| 2003/0236568 A1 | 12/2003 | Hojeibane et al. |
| 2004/0019374 A1 | 1/2004 | Hojeibane et al. |
| 2004/0034411 A1 | 2/2004 | Quijano et al. |
| 2004/0106976 A1 | 6/2004 | Bailey et al. |
| 2004/0122514 A1 | 6/2004 | Fogarty et al. |
| 2004/0122516 A1 | 6/2004 | Fogarty et al. |
| 2004/0167573 A1 | 8/2004 | Williamson et al. |
| 2004/0186563 A1 | 9/2004 | Iobbi |
| 2004/0186565 A1 | 9/2004 | Schreck |
| 2004/0206363 A1 | 10/2004 | McCarthy et al. |
| 2004/0210304 A1 | 10/2004 | Seguin et al. |
| 2004/0210305 A1 | 10/2004 | Shu et al. |
| 2004/0210307 A1 | 10/2004 | Khairkhahan |
| 2004/0225355 A1 | 11/2004 | Stevens |
| 2004/0236411 A1 | 11/2004 | Sarac et al. |
| 2004/0260390 A1 | 12/2004 | Sarac et al. |
| 2005/0010285 A1 | 1/2005 | Lambrecht et al. |
| 2005/0027348 A1 | 2/2005 | Case et al. |
| 2005/0033398 A1 | 2/2005 | Seguin |
| 2005/0043760 A1 | 2/2005 | Fogarty et al. |
| 2005/0043790 A1 | 2/2005 | Seguin |
| 2005/0060029 A1 | 3/2005 | Le et al. |
| 2005/0065594 A1 | 3/2005 | DiMatteo et al. |
| 2005/0065614 A1 | 3/2005 | Stinson |
| 2005/0075584 A1 | 4/2005 | Cali |
| 2005/0075713 A1 | 4/2005 | Biancucci et al. |
| 2005/0075717 A1 | 4/2005 | Nguyen et al. |
| 2005/0075718 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0080454 A1 | 4/2005 | Drews et al. |
| 2005/0096738 A1 | 5/2005 | Cali et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137694 A1 | 6/2005 | Haug et al. |
| 2005/0137695 A1 | 6/2005 | Salahieh et al. |
| 2005/0165477 A1 | 7/2005 | Anduiza et al. |
| 2005/0165479 A1 | 7/2005 | Drews et al. |
| 2005/0182483 A1 | 8/2005 | Osborne et al. |
| 2005/0182486 A1 | 8/2005 | Gabbay |
| 2005/0192665 A1 | 9/2005 | Spenser et al. |
| 2005/0203616 A1 | 9/2005 | Cribier |
| 2005/0203617 A1 | 9/2005 | Forster et al. |
| 2005/0222674 A1 | 10/2005 | Paine |
| 2005/0234546 A1 | 10/2005 | Nugent et al. |
| 2005/0240259 A1 | 10/2005 | Sisken et al. |
| 2005/0251252 A1 | 11/2005 | Stobie |
| 2005/0283231 A1 | 12/2005 | Haug et al. |
| 2006/0025857 A1 | 2/2006 | Bergheim et al. |
| 2006/0052867 A1 | 3/2006 | Revuelta et al. |
| 2006/0058872 A1 | 3/2006 | Salahieh et al. |
| 2006/0074484 A1 | 4/2006 | Huber |
| 2006/0085060 A1 | 4/2006 | Campbell |
| 2006/0122634 A1 | 6/2006 | Ino et al. |
| 2006/0122692 A1 | 6/2006 | Gilad et al. |
| 2006/0149360 A1 | 7/2006 | Schwammenthal et al. |
| 2006/0161249 A1 | 7/2006 | Realyvasquez et al. |
| 2006/0195183 A1 | 8/2006 | Navia et al. |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0229708 A1 | 10/2006 | Powell et al. |
| 2006/0235508 A1 | 10/2006 | Lane et al. |
| 2006/0241745 A1 | 10/2006 | Solem |
| 2006/0253191 A1 | 11/2006 | Salahieh et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0271172 A1 | 11/2006 | Tehrani |
| 2006/0271175 A1 | 11/2006 | Woolfson et al. |
| 2006/0287717 A1 | 12/2006 | Rowe et al. |
| 2006/0293745 A1 | 12/2006 | Carpentier et al. |
| 2007/0010876 A1 | 1/2007 | Salahieh et al. |
| 2007/0010877 A1 | 1/2007 | Salahieh et al. |
| 2007/0016285 A1 | 1/2007 | Lane et al. |
| 2007/0016286 A1 | 1/2007 | Herrmann et al. |
| 2007/0016288 A1 | 1/2007 | Gurskis et al. |
| 2007/0043435 A1 | 2/2007 | Seguin et al. |
| 2007/0078509 A1 | 4/2007 | Lotfy |
| 2007/0078510 A1 | 4/2007 | Ryan |
| 2007/0100421 A1 | 5/2007 | Griffin |
| 2007/0100440 A1 | 5/2007 | Figulla et al. |
| 2007/0129794 A1 | 6/2007 | Realyvasquez |
| 2007/0142907 A1 | 6/2007 | Moaddeb et al. |
| 2007/0150053 A1 | 6/2007 | Gurskis et al. |
| 2007/0156233 A1 | 7/2007 | Kapadia et al. |
| 2007/0162103 A1 | 7/2007 | Case et al. |
| 2007/0162111 A1 | 7/2007 | Fukamachi et al. |
| 2007/0203575 A1 | 8/2007 | Forster et al. |
| 2007/0203576 A1 | 8/2007 | Lee et al. |
| 2007/0213813 A1 | 9/2007 | Von Segesser et al. |
| 2007/0225801 A1 | 9/2007 | Drews et al. |
| 2007/0239269 A1 | 10/2007 | Dolan et al. |
| 2007/0244546 A1 | 10/2007 | Francis |
| 2007/0260305 A1 | 11/2007 | Drews et al. |
| 2007/0265701 A1 | 11/2007 | Gurskis et al. |
| 2007/0270751 A1 | 11/2007 | Stangenes et al. |
| 2007/0270944 A1 | 11/2007 | Bergheim et al. |
| 2007/0282436 A1 | 12/2007 | Pinchuk |
| 2008/0021546 A1 | 1/2008 | Patz et al. |
| 2008/0033543 A1 | 2/2008 | Gurskis et al. |
| 2008/0033570 A1* | 2/2008 | Blitz ................... A61F 2/958 604/103.05 |
| 2008/0065011 A1 | 3/2008 | Marchand et al. |
| 2008/0082161 A1 | 4/2008 | Woo |
| 2008/0119875 A1 | 5/2008 | Ino et al. |
| 2008/0154356 A1 | 6/2008 | Obermiller et al. |
| 2008/0281411 A1 | 11/2008 | Berreklouw |
| 2009/0036903 A1 | 2/2009 | Ino et al. |
| 2009/0138079 A1 | 5/2009 | Tuval et al. |
| 2009/0192518 A1 | 7/2009 | Golden et al. |
| 2009/0192602 A1 | 7/2009 | Kuehn |
| 2009/0192603 A1 | 7/2009 | Kuehn |
| 2009/0192604 A1 | 7/2009 | Gloss |
| 2009/0192605 A1 | 7/2009 | Gloss et al. |
| 2009/0192606 A1 | 7/2009 | Gloss et al. |

(56) References Cited

U.S. PATENT DOCUMENTS

| | | |
|---|---|---|
| 2010/0161036 A1 | 6/2010 | Pintor et al. |
| 2010/0234940 A1 | 9/2010 | Dolan |
| 2010/0249894 A1* | 9/2010 | Oba ............... A61F 2/2418 623/2.18 |
| 2010/0249908 A1 | 9/2010 | Chau et al. |
| 2010/0292784 A1 | 11/2010 | Giannetti et al. |
| 2010/0331972 A1 | 12/2010 | Pintor et al. |
| 2011/0022165 A1 | 1/2011 | Oba et al. |
| 2011/0066234 A1 | 3/2011 | Gordon et al. |
| 2011/0098804 A1 | 4/2011 | Yeung et al. |
| 2011/0147251 A1 | 6/2011 | Hodshon et al. |
| 2011/0245917 A1 | 10/2011 | Savage et al. |
| 2012/0022633 A1 | 1/2012 | Olson et al. |
| 2012/0065729 A1 | 3/2012 | Pintor et al. |
| 2012/0078357 A1 | 3/2012 | Conklin |
| 2012/0083875 A1 | 4/2012 | Johnson et al. |
| 2012/0150288 A1 | 6/2012 | Hodshon et al. |
| 2013/0018449 A1 | 1/2013 | Bailey et al. |
| 2013/0053949 A1 | 2/2013 | Pintor et al. |
| 2013/0116777 A1 | 5/2013 | Pintor et al. |
| 2013/0190862 A1 | 7/2013 | Pintor et al. |

FOREIGN PATENT DOCUMENTS

| | | |
|---|---|---|
| EP | 0125393 A1 | 11/1984 |
| EP | 0143246 A2 | 6/1985 |
| EP | 0179562 A1 | 4/1986 |
| EP | 1171059 A1 | 1/2002 |
| EP | 2250976 A1 | 11/2010 |
| GB | 414443 A | 8/1934 |
| GB | 2056023 A | 3/1981 |
| GB | 2 069 843 A | 9/1981 |
| GB | 2254254 A | 10/1992 |
| GB | 2 279 134 A | 12/1994 |
| SU | 1116573 A1 | 7/1985 |
| SU | 1697790 A1 | 12/1991 |
| WO | 8900840 A1 | 2/1989 |
| WO | 9115167 A1 | 10/1991 |
| WO | 9212690 A1 | 8/1992 |
| WO | 9213502 A1 | 8/1992 |
| WO | 9219184 A1 | 11/1992 |
| WO | 9219185 A1 | 11/1992 |
| WO | 9517139 A1 | 6/1995 |
| WO | 9528899 A1 | 11/1995 |
| WO | 9640006 A1 | 12/1996 |
| WO | 9709933 A1 | 3/1997 |
| WO | 9709944 A1 | 3/1997 |
| WO | 9727799 A1 | 8/1997 |
| WO | 9741801 A1 | 11/1997 |
| WO | 9742871 A1 | 11/1997 |
| WO | 9806329 A1 | 2/1998 |
| WO | 9911201 A2 | 3/1999 |
| WO | 9915112 A1 | 4/1999 |
| WO | 9951169 A1 | 10/1999 |
| WO | 0032105 A1 | 6/2000 |
| WO | 0040176 A1 | 7/2000 |
| WO | 0060995 A2 | 10/2000 |
| WO | 0154624 A1 | 8/2001 |
| WO | 0154625 A1 | 8/2001 |
| WO | 02076347 | 10/2002 |
| WO | 2006086135 A2 | 8/2006 |
| WO | 2006127756 A2 | 11/2006 |
| WO | 2013028387 A2 | 2/2013 |

OTHER PUBLICATIONS

Sadowski, Jerzy; Kapelak, Boguslaw; Bartus, Krzysztof, "Sutureless Heart Valve Implantation—A Case Study," Touch Briefings, 2005, pp. 48-50.

* cited by examiner

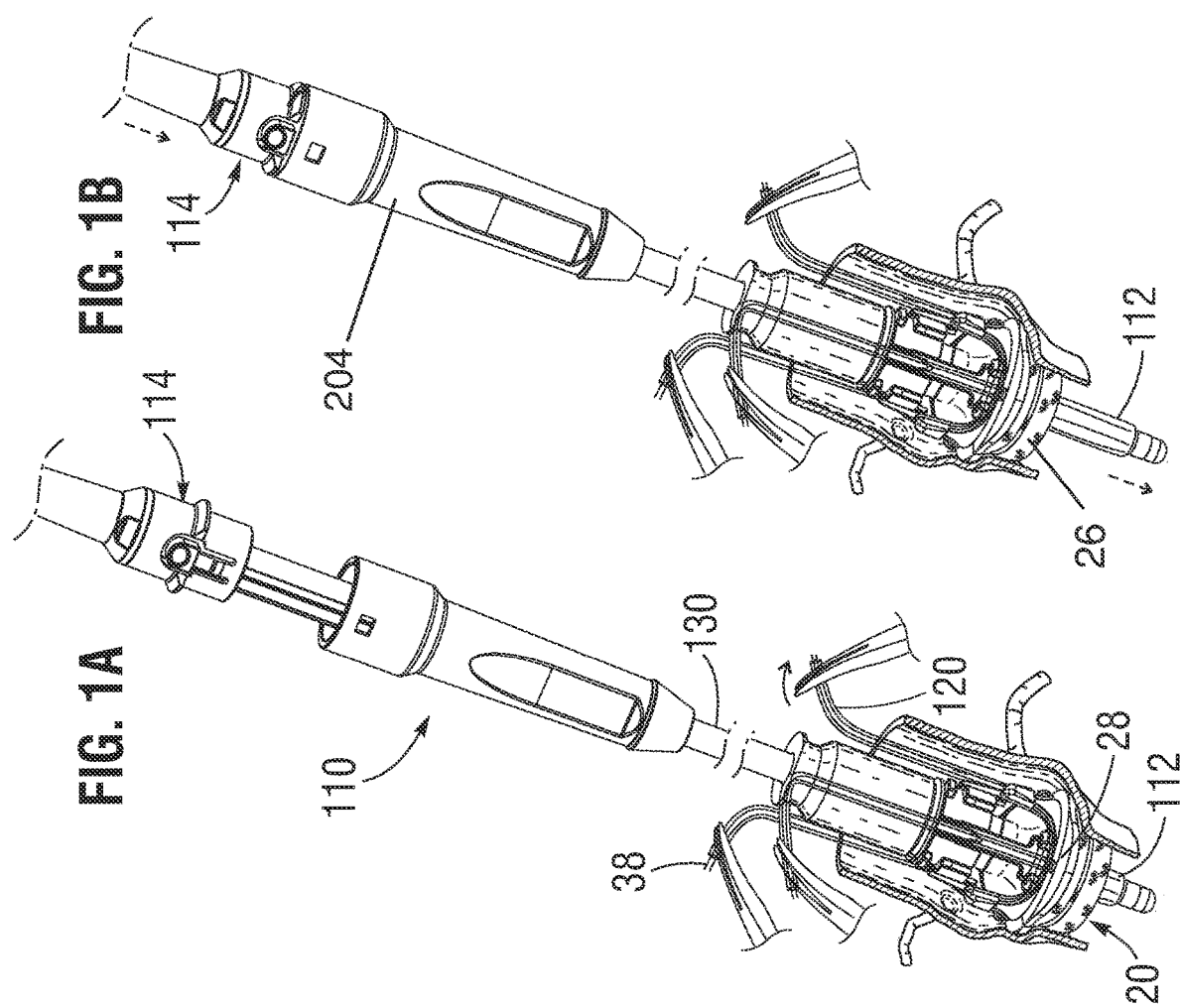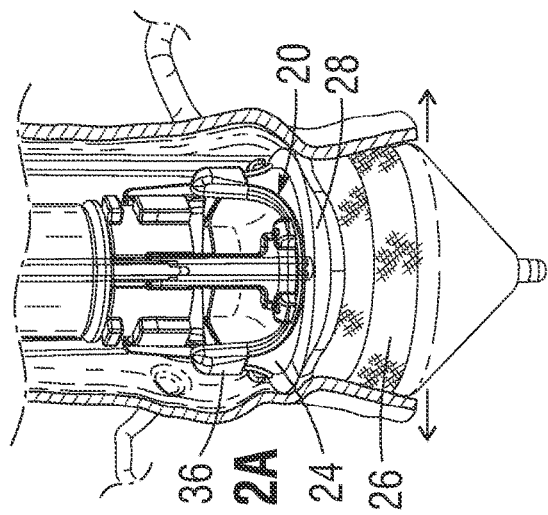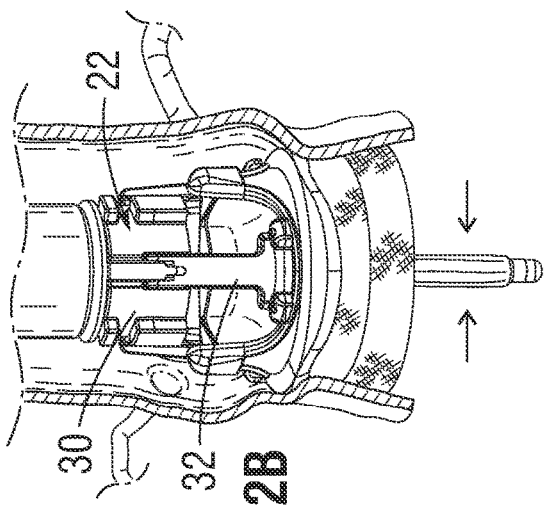

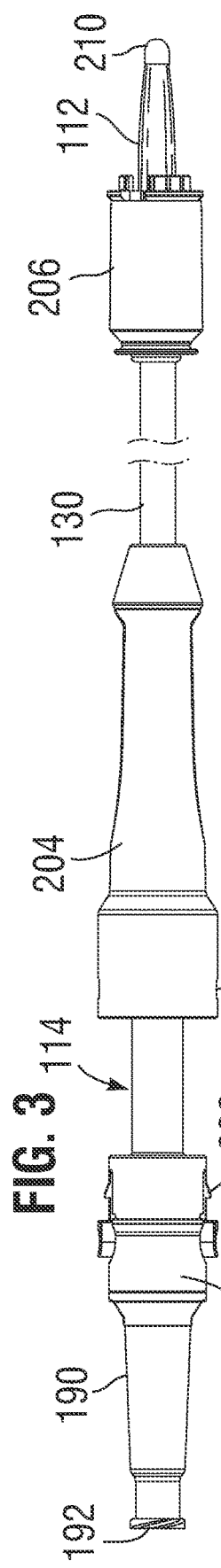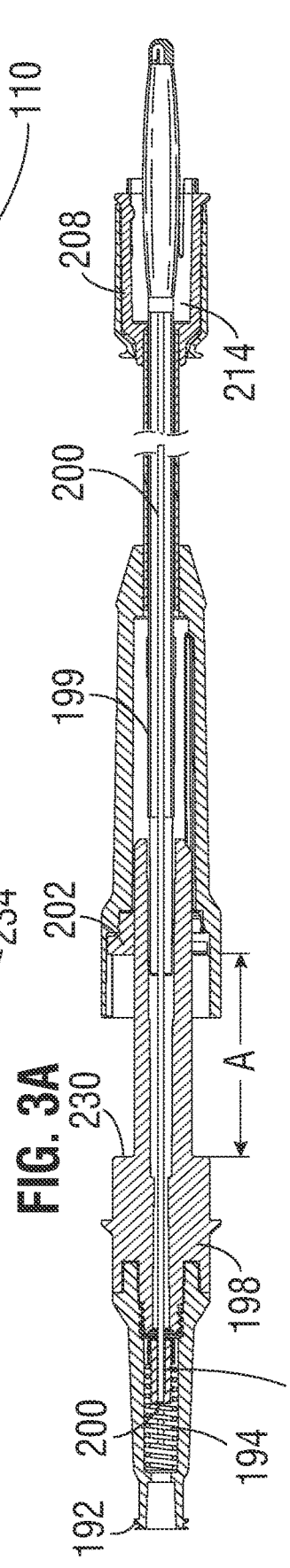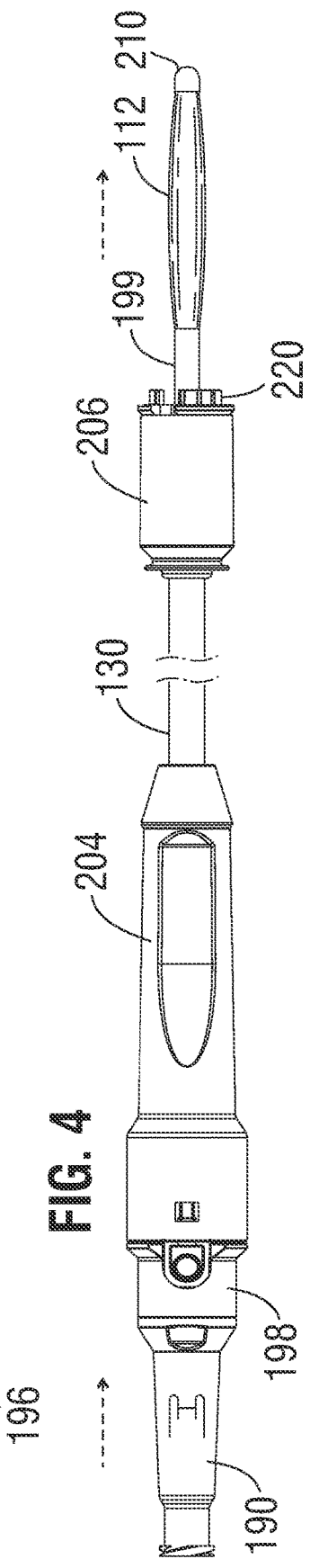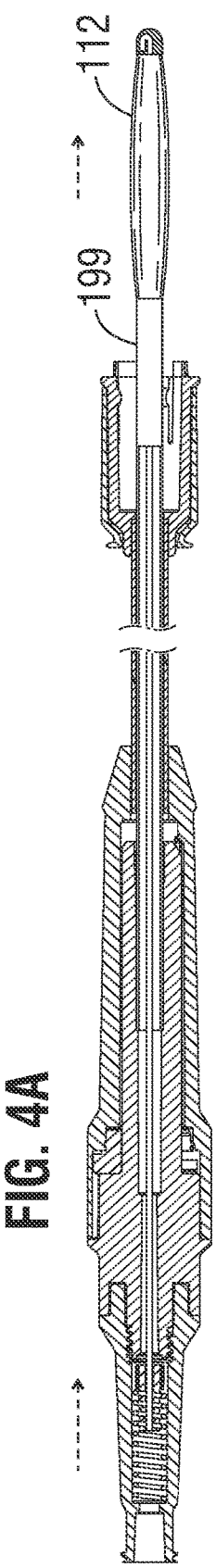

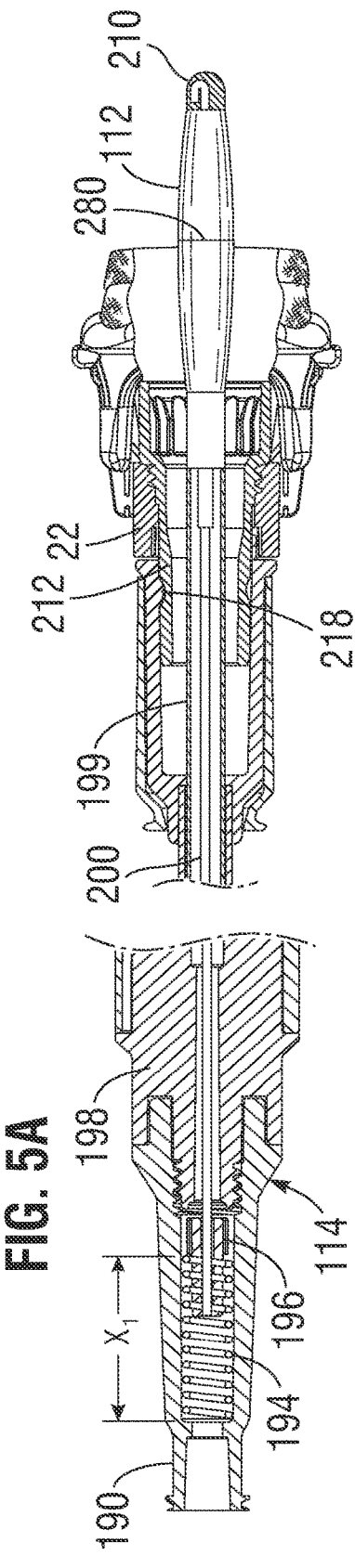
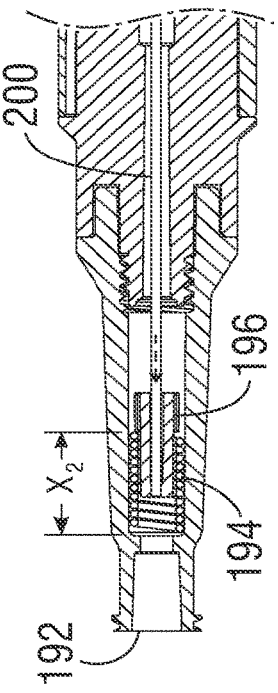
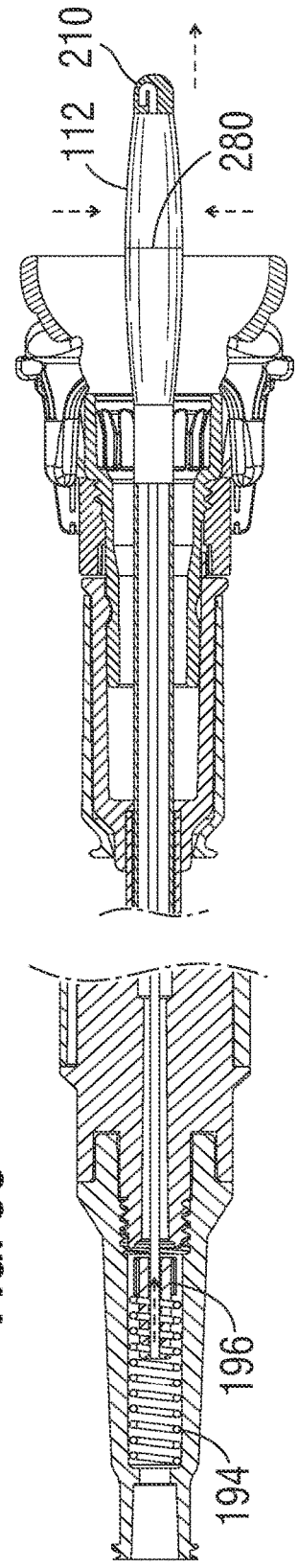
FIG. 5A
FIG. 5B
FIG. 5C

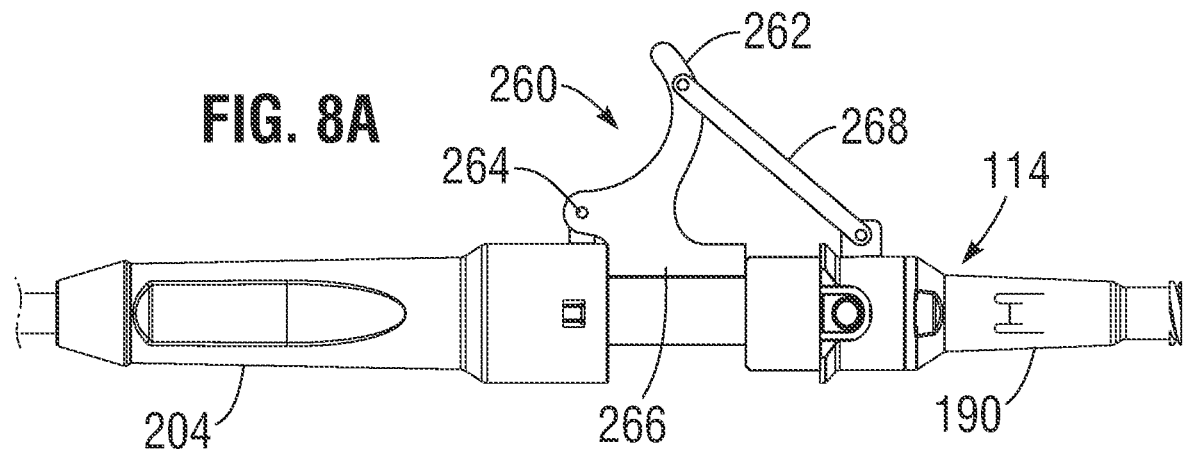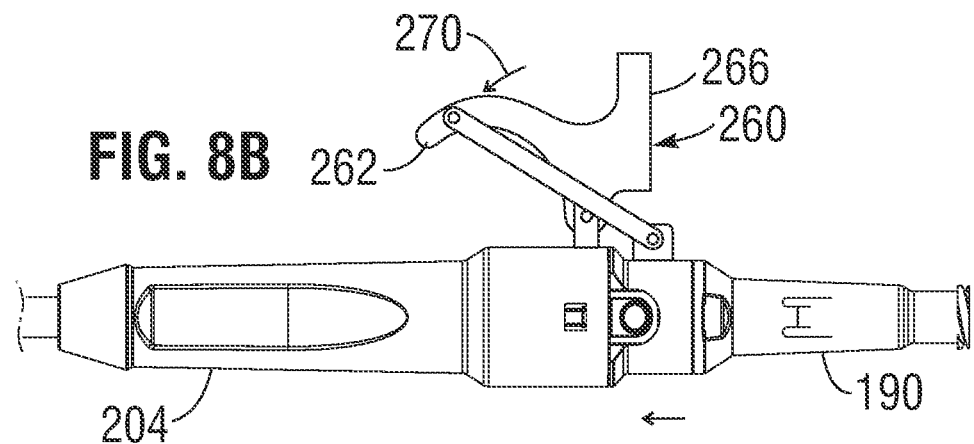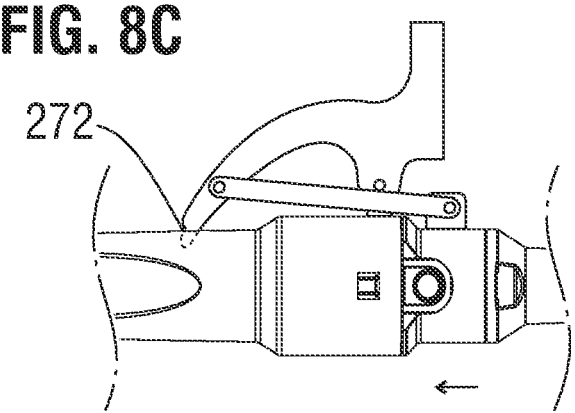

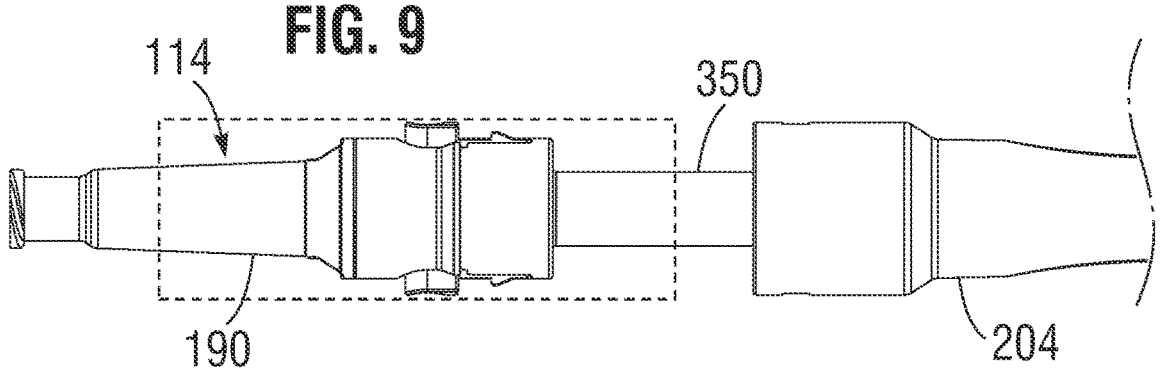
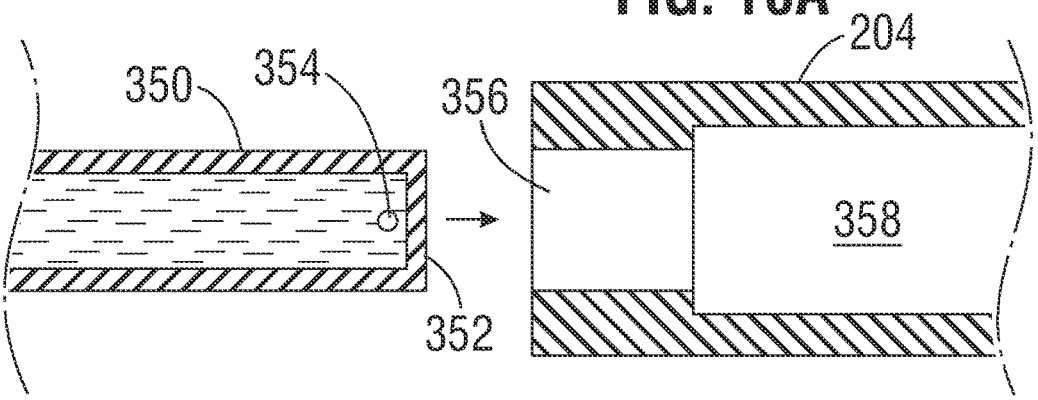
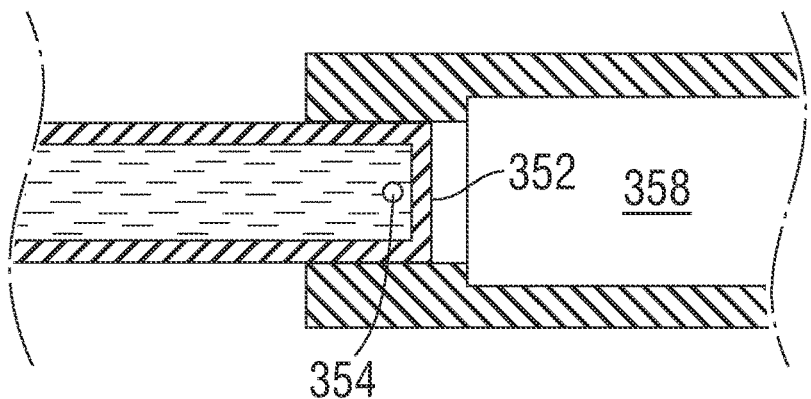
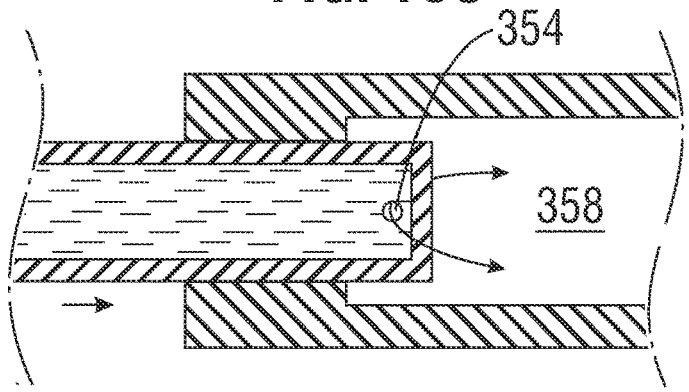

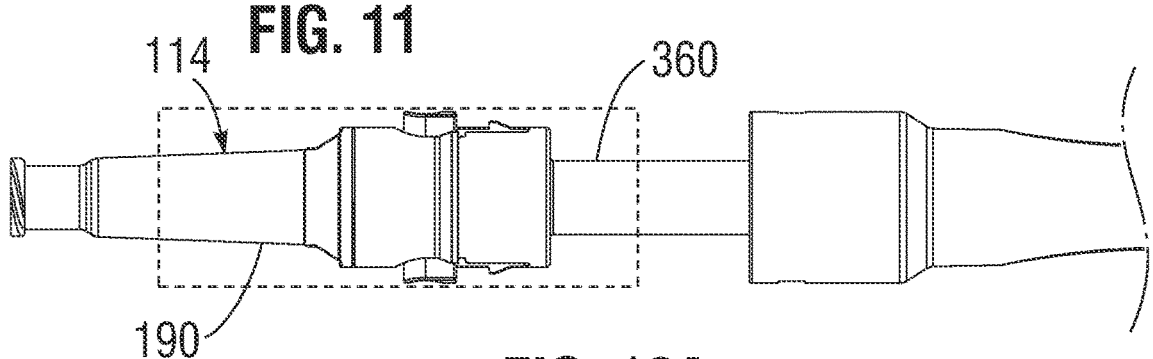
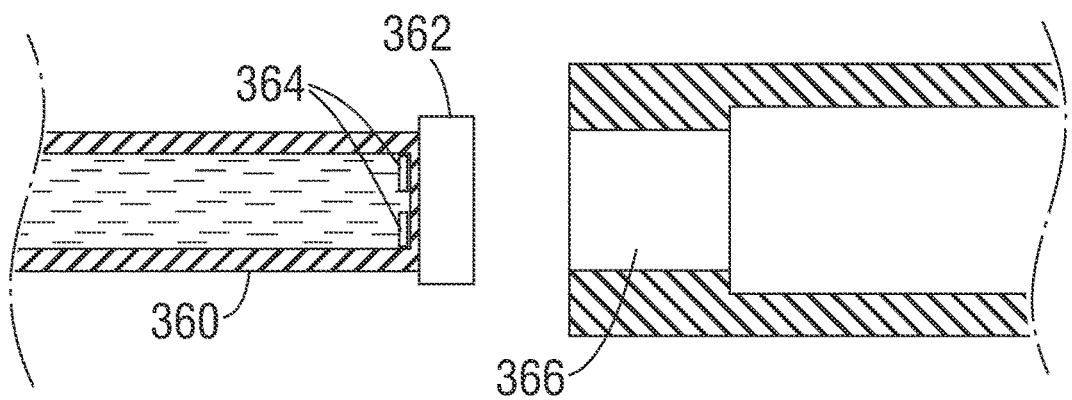
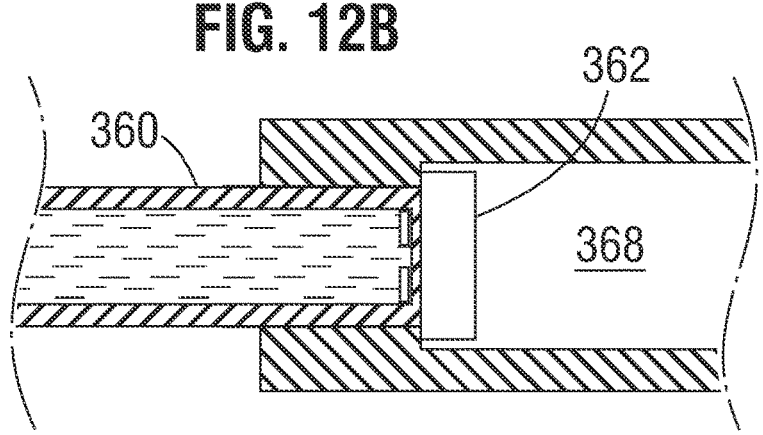
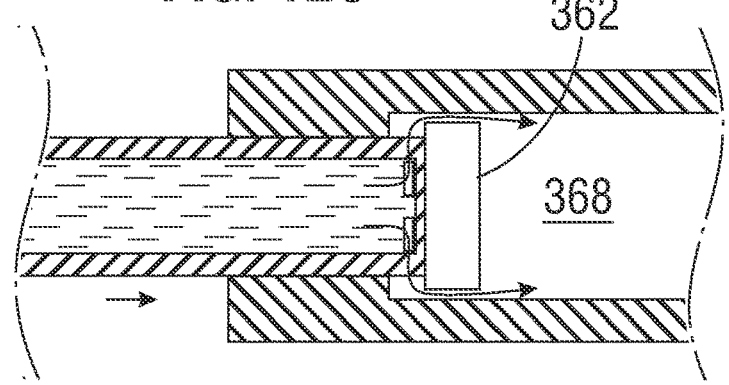

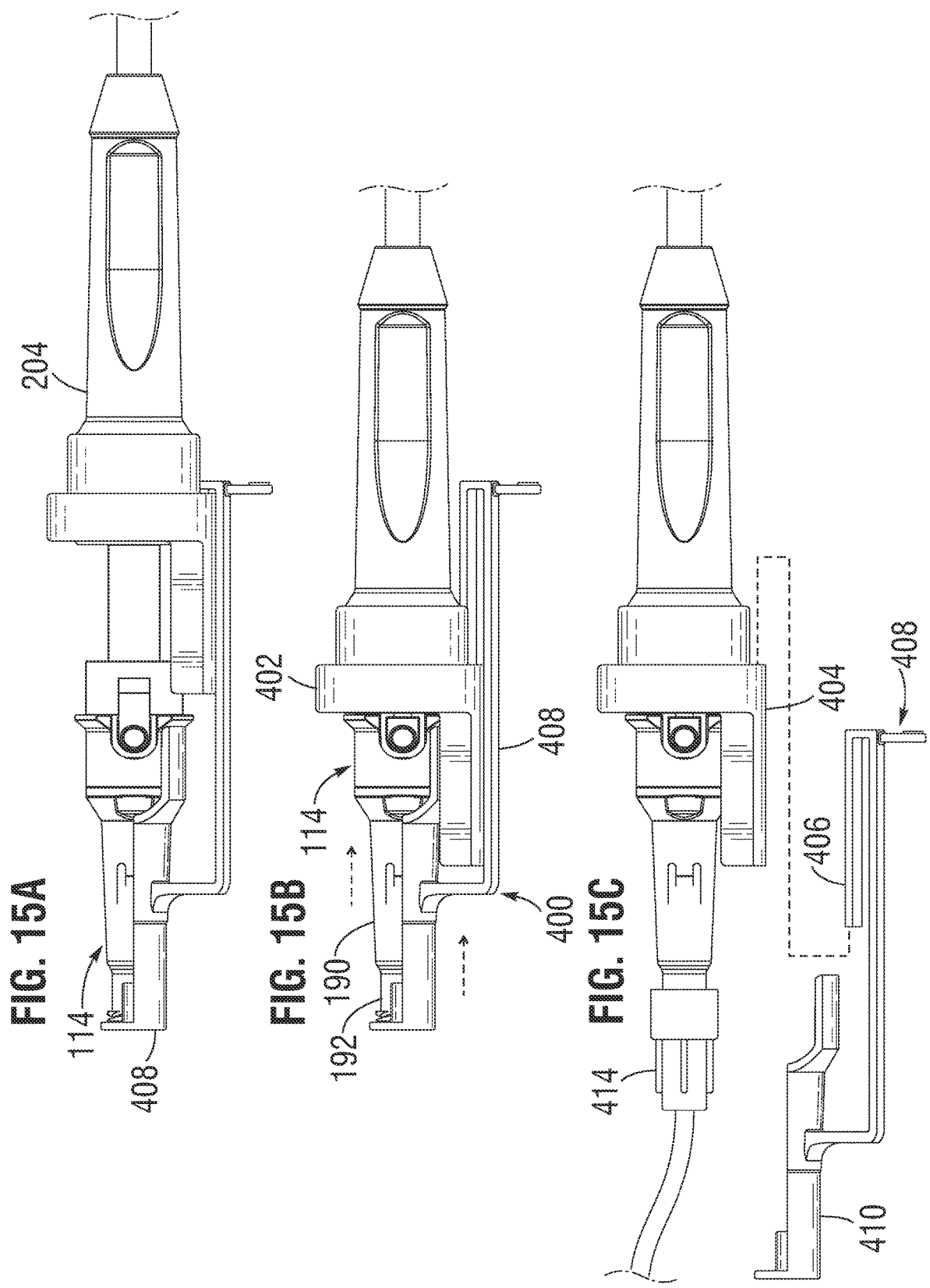

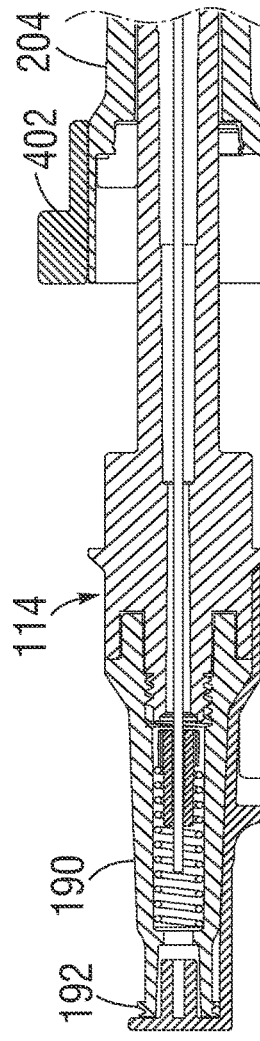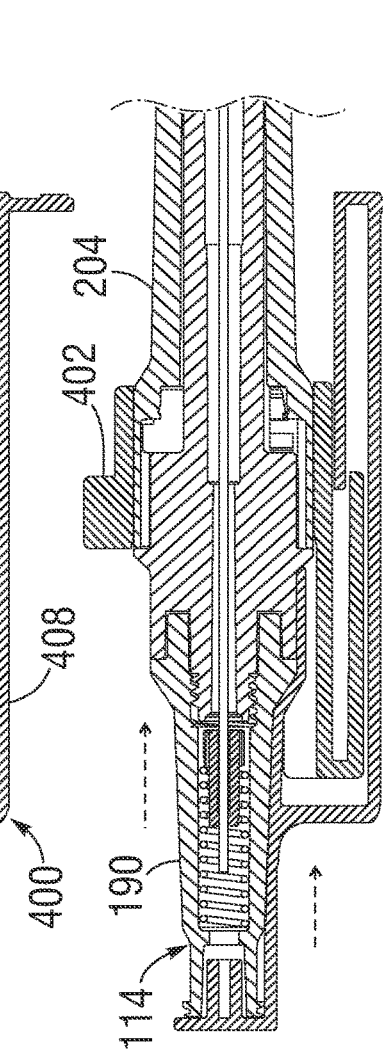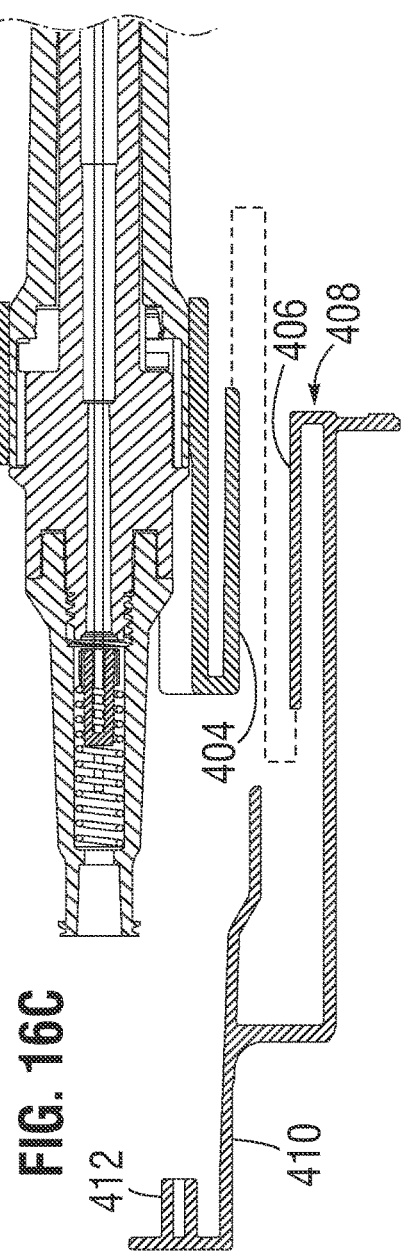

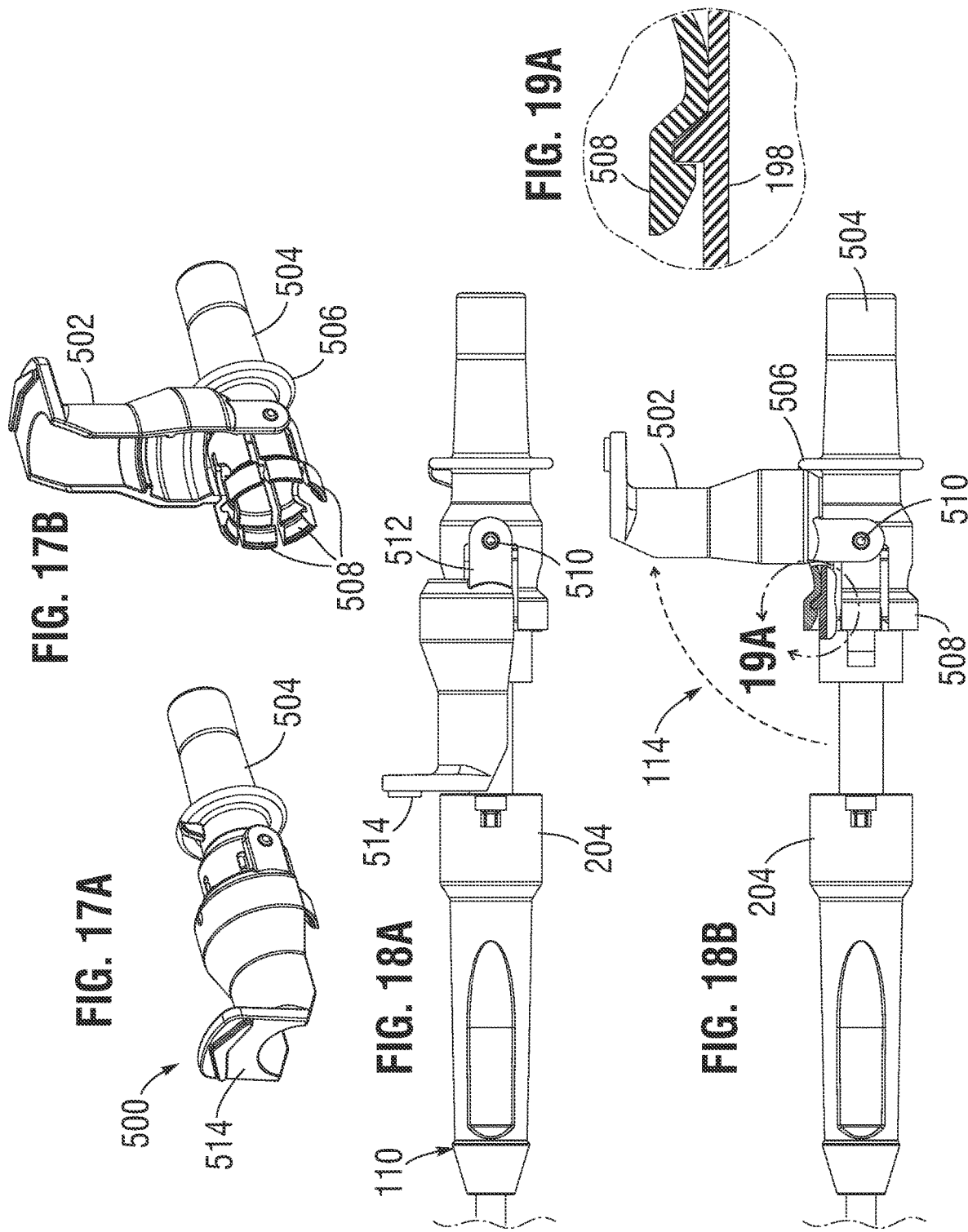

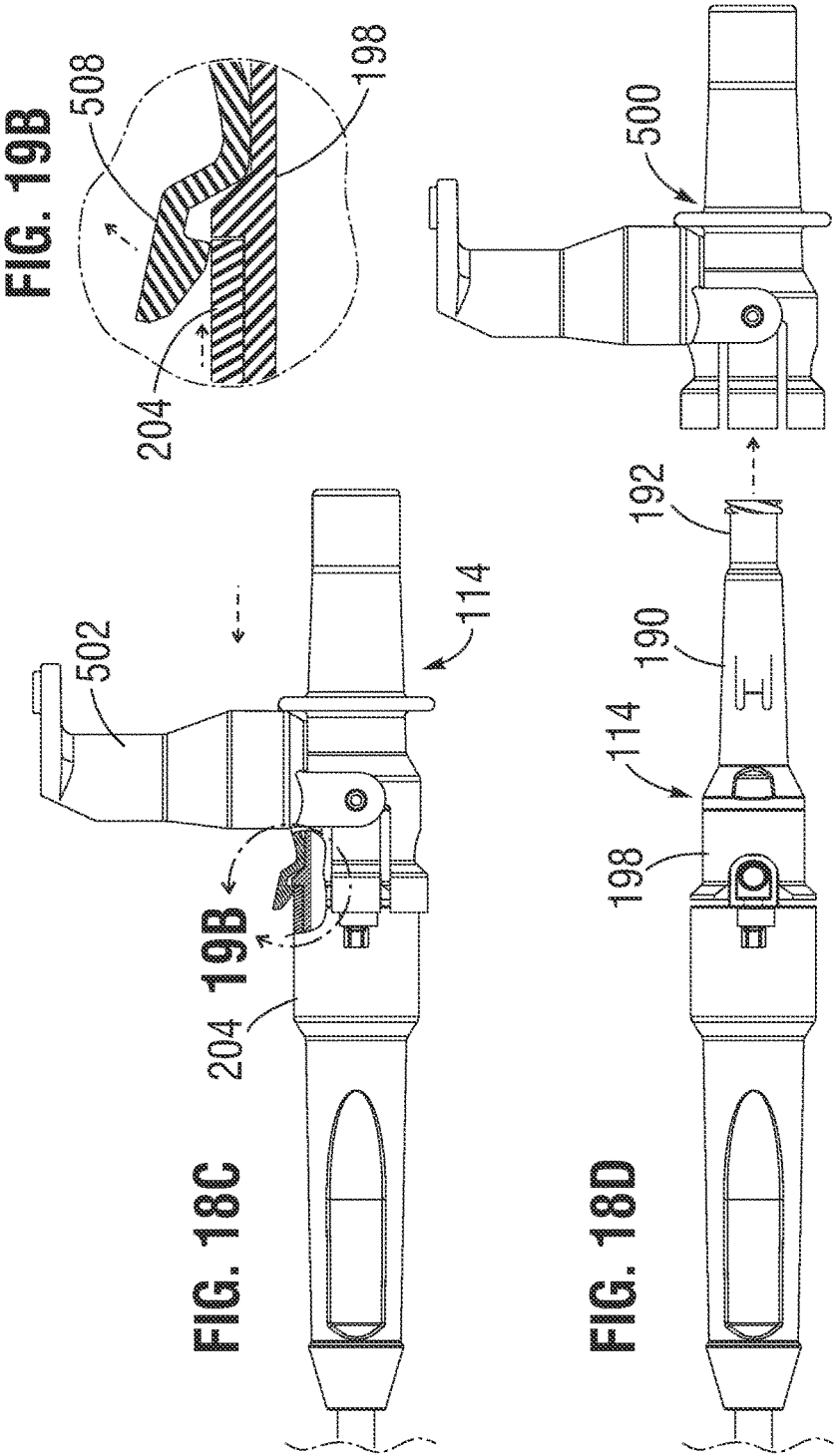

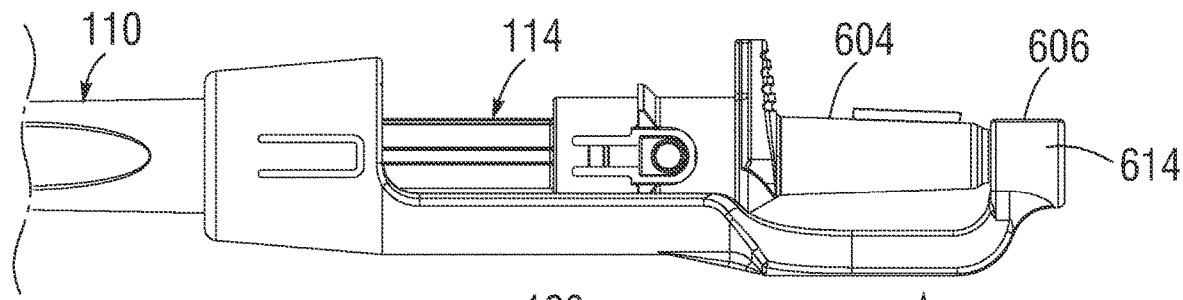
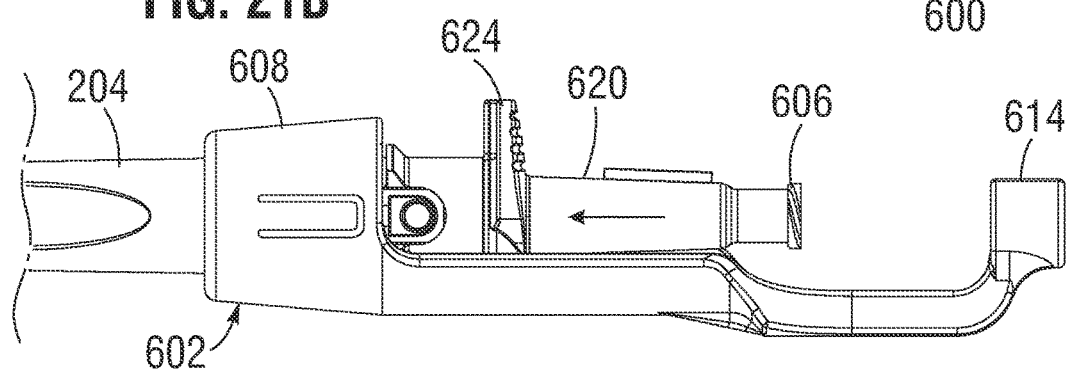
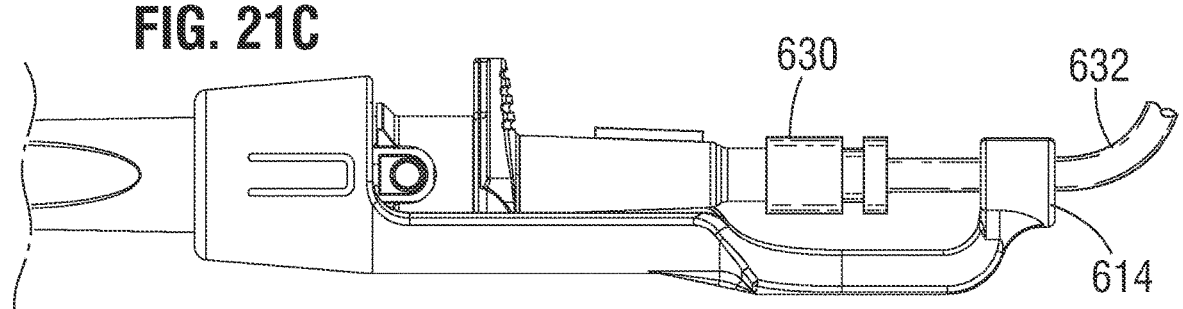
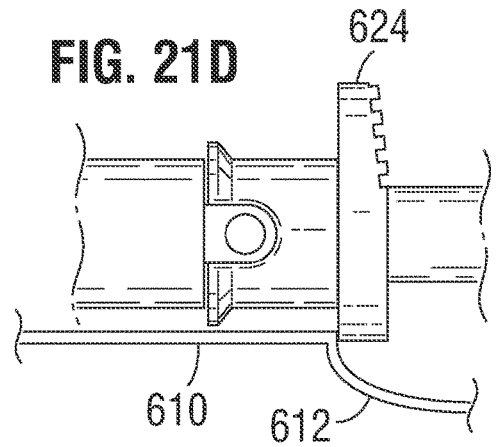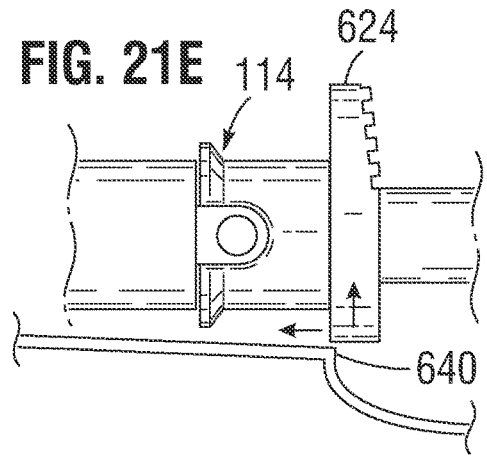

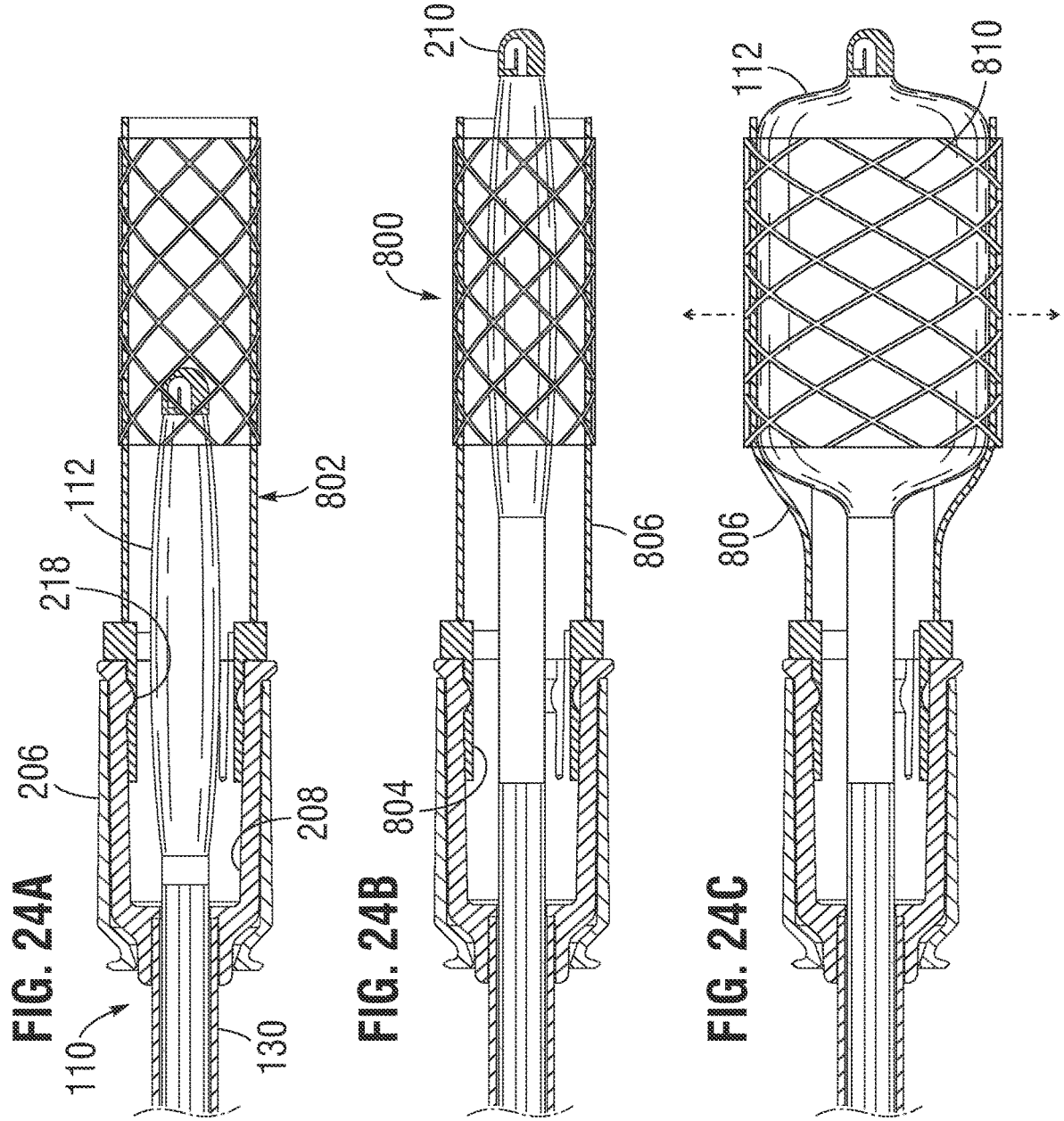

METHODS OF SAFELY EXPANDING PROSTHETIC HEART VALVES

CROSS REFERENCE TO RELATED APPLICATIONS

This application is a continuation of U.S. patent application Ser. No. 16/779,429, filed Jan. 31, 2020, now U.S. Pat. No. 11,197,757, which is a divisional of U.S. patent application Ser. No. 15/368,335, filed Dec. 2, 2016, now U.S. Pat. No. 10,548,728, which is a continuation of U.S. patent application Ser. No. 14/847,190, filed Sep. 8, 2015, now U.S. Pat. No. 9,968,450, which is a divisional of U.S. patent application Ser. No. 13/797,572, filed Mar. 12, 2013, now U.S. Pat. No. 9,125,741, which is a continuation-in-part of U.S. patent application Ser. No. 13/167,639, filed Jun. 23, 2011, now U.S. Pat. No. 8,641,757, which claims the benefit of U.S. Patent Application No. 61/381,931 filed Sep. 10, 2010, the entire contents all of which are incorporated by reference for all purposes.

FIELD OF THE INVENTION

The present invention generally relates to prosthetic valves for implantation in body channels. More particularly, the present invention relates to unitary surgical prosthetic heart valves configured to be surgically implanted in less time than current valves, and associated valve delivery methods.

BACKGROUND OF THE INVENTION

In vertebrate animals, the heart is a hollow muscular organ having four pumping chambers—the left and right atria and the left and right ventricles, each provided with its own one-way valve. The natural heart valves are identified as the aortic, mitral (or bicuspid), tricuspid and pulmonary, and are each mounted in an annulus comprising dense fibrous rings attached either directly or indirectly to the atrial and ventricular muscle fibers. Each annulus defines a flow orifice.

The atria are the blood-receiving chambers, which pump blood into the ventricles. The ventricles are the blood-discharging chambers. A wall composed of fibrous and muscular parts, called the interatrial septum separates the right and left atria. The fibrous interatrial septum is a materially stronger tissue structure compared to the more friable muscle tissue of the heart. An anatomic landmark on the interatrial septum is an oval, thumbprint sized depression called the oval fossa, or fossa ovalis.

The synchronous pumping actions of the left and right sides of the heart constitute the cardiac cycle. The cycle begins with a period of ventricular relaxation, called ventricular diastole. The cycle ends with a period of ventricular contraction, called ventricular systole. The four valves ensure that blood does not flow in the wrong direction during the cardiac cycle; that is, to ensure that the blood does not back flow from the ventricles into the corresponding atria, or back flow from the arteries into the corresponding ventricles. The mitral valve is between the left atrium and the left ventricle, the tricuspid valve between the right atrium and the right ventricle, the pulmonary valve is at the opening of the pulmonary artery, and the aortic valve is at the opening of the aorta.

The anterior portion of the mitral valve annulus abuts the non-coronary leaflet of the aortic valve. The mitral valve annulus is in the vicinity of the circumflex branch of the left coronary artery, and the posterior side is near the coronary sinus and its tributaries.

Various surgical techniques may be used to repair a diseased or damaged valve. In a valve replacement operation, the damaged leaflets are excised and the annulus sculpted to receive a replacement valve. Due to aortic stenosis and other heart valve diseases, thousands of patients undergo surgery each year wherein the defective native heart valve is replaced by a prosthetic valve, either bioprosthetic or mechanical. Another less drastic method for treating defective valves is through repair or reconstruction, which is typically used on minimally calcified valves. The problem with surgical therapy is the significant insult it imposes on these chronically ill patients with high morbidity and mortality rates associated with surgical repair.

When the valve is replaced, surgical implantation of the prosthetic valve typically requires an open-chest surgery during which the heart is stopped and patient placed on cardiopulmonary bypass (a so-called "heart-lung machine"). In one common surgical procedure, the diseased native valve leaflets are excised and a prosthetic valve is sutured to the surrounding tissue at the valve annulus. Because of the trauma associated with the procedure and the attendant duration of extracorporeal blood circulation, some patients do not survive the surgical procedure or die shortly thereafter. It is well known that the risk to the patient increases with the amount of time required on extracorporeal circulation. Due to these risks, a substantial number of patients with defective valves are deemed inoperable because their condition is too frail to withstand the procedure. By some estimates, about 30 to 50% of the subjects suffering from aortic stenosis who are older than 80 years cannot be operated on for aortic valve replacement.

Because of the drawbacks associated with conventional open-heart surgery, percutaneous and minimally-invasive surgical approaches are garnering intense attention. In one technique, a prosthetic valve is configured to be implanted in a much less invasive procedure by way of catheterization. For instance, U.S. Pat. No. 5,411,552 to Andersen et al. describes a collapsible valve percutaneously introduced in a compressed state through a catheter and expanded in the desired position by balloon inflation. Although these remote implantation techniques have shown great promise for treating certain patients, replacing a valve via surgical intervention is still the preferred treatment procedure. One hurdle to the acceptance of remote implantation is resistance from doctors who are understandably anxious about converting from an effective, if imperfect, regimen to a novel approach that promises great outcomes but is relatively foreign. In conjunction with the understandable caution exercised by surgeons in switching to new techniques of heart valve replacement, regulatory bodies around the world are moving slowly as well. Numerous successful clinical trials and follow-up studies are in process, but much more experience with these new technologies will be required before they are completely accepted.

Accordingly, there is a need for an improved device and associated method of use wherein a prosthetic valve can be surgically implanted in a body channel in a more efficient procedure that reduces the time required on extracorporeal circulation. It is desirable that such a device and method be capable of helping patients with defective valves that are deemed inoperable because their condition is too frail to withstand a lengthy conventional surgical procedure.

Furthermore, surgeons relate that one of the most difficult tasks when attempting minimally invasive heart valve implantation or implantation through a small incision is tying the suture knots that hold the valve in position. A typical aortic valve implant utilizes 12-24 sutures (commonly 15) distributed evenly around and manually tied on one side of the sewing ring. The knots directly behind the commissure posts of a prosthetic aortic valve are particularly challenging because of space constraints Eliminating the need to tie suture knots or even reducing the number of knots to those that are more accessible would greatly facilitate the use of smaller incisions that reduces infection risk, reduces the need for blood transfusions and allows more rapid recovery compared to patients whose valves are implanted through the full sternotomy commonly used for heart valve implantation.

The present invention addresses these needs and others.

SUMMARY OF THE INVENTION

Various embodiments of the present application provide prosthetic valves and methods of use for replacing a defective native valve in a human heart. Certain embodiments are particularly well adapted for use in a surgical procedure for quickly and easily replacing a heart valve while minimizing time using extracorporeal circulation (i.e., bypass pump).

In one embodiment, a method for treating a native aortic valve in a human heart to replace the function of the aortic valve, comprises: 1) accessing a native valve through an opening in a chest; 2) placing guiding sutures in the annulus 3) advancing a heart valve within a lumen of the annulus; and 4) plastically expanding a metallic anchoring skirt on the heart valve to mechanically couple to the annulus in a quick and efficient manner.

The present application contemplates various means for physically preventing movement of the balloon catheter, preferably coupled with a visual reminder not to deploy the catheter prematurely. Furthermore, exemplary heart valve delivery systems also preferably have devices that prevent premature inflation of a dilatation balloon until the balloon catheter has been properly advanced.

The exemplary heart valves are a hybrid valve that includes a prosthetic valve having an inner frame assembly defining a non-expandable, non-collapsible orifice, and an expandable frame extending from an inflow end thereof, the expandable frame having a contracted state for delivery to an implant position and an expanded state;

For example, one system for delivering the exemplary hybrid prosthetic heart valve comprises a valve holder attached to the heart valve and having a bore, and an elongated handle shaft attached to a proximal end of the valve holder and having a lumen, a proximal end of the handle shaft having a handpiece. An expansion catheter extends through the handle shaft, has an expandable member on a distal end sized to pass through the bore of the valve holder, and a proximal end projecting proximally from out of the handpiece. The expansion catheter moves axially relative to the handle shaft between a retracted position and an advanced position in which the expandable member is located within the expandable frame of the heart valve. Finally, the system includes a safety member engaged between the expansion catheter and the handle shaft that prevents distal movement of the expansion catheter from its retracted position.

In one form, the expansion catheter is a balloon catheter with a luer connector, and the safety member comprises a locking clip that snaps onto the handpiece and proximal end of the expansion catheter and prevents relative balloon catheter handpiece movement prior to removal. The expansion catheter may be a balloon catheter and the expandable member is a balloon wherein a proximal end of the balloon catheter has a luer connector, wherein the locking clip covers the luer connector and prevents balloon inflation prior to removal. Alternatively, the safety member comprises a safety guard that snaps onto a proximal end of the balloon catheter and has a toggle lever that pivots to a position between the balloon catheter and the proximal end of the handpiece, wherein outward pivoting of the toggle lever permits distal movement of the balloon catheter, and distal movement of the balloon catheter and attached safety guard enables removal of the safety guard so as to prevent balloon inflation prior to distal movement of the balloon catheter.

Another disclosed system for delivering an exemplary hybrid prosthetic heart valve includes a valve holder attached to the heart valve and having a bore, and an integrated assembly of a handle shaft and balloon catheter. The assembly has a handle shaft with a handpiece on a proximal end and a distal adapter configured to mate with a proximal end of the valve holder. The axial positions of the handpiece and adapter are fixed, and the handle shaft and handpiece define a handle lumen. A balloon catheter having a balloon is received within the handle lumen and has a proximal balloon displacer for manually displacing the catheter relative to the handle lumen and a proximal luer connector for attaching a fluid fill tube to inflate the balloon. The balloon catheter has two primary positions relative to the handpiece—a retracted position wherein the balloon displacer is spaced from the handpiece and the balloon resides partly within the handle shaft adapter and an advanced position where the balloon displacer engages the handpiece and the balloon extends distally from the handle shaft adapter and is positioned within the expandable frame. A safety member engaged between the balloon catheter and the handpiece prevents distal movement of the balloon catheter from its retracted position.

A preferred method of delivery and implant of a hybrid prosthetic heart valve system comprises:

providing a delivery system including a handle shaft having a lumen therethrough, and wherein an expansion catheter extends through the handle shaft and has an expandable member on a distal end and a proximal end projecting proximally from out of the handle shaft, the expansion catheter being capable of linear movement relative to the handle shaft;

providing a hybrid heart valve with a valve member and expandable frame;

advancing the delivery system so that the heart valve with the frame in its contracted state is located at an implant position adjacent the annulus;

displacing a safety member from engagement between a portion of the expansion catheter that projects from the handle shaft and a proximal end of the handle shaft, the safety member preventing distal movement of the expansion catheter relative to the handle shaft prior to displacement;

displacing the expansion catheter distally so that the expandable member is located within the heart valve frame; and expanding the expandable member to expand the frame.

The safety member may comprise a locking clip that snaps onto the handpiece and proximal end of the expansion catheter preventing relative balloon catheter handpiece movement prior to removal, wherein the method includes removing the locking clip prior to the step of displacing the expansion catheter distally. If the expansion catheter is a balloon catheter with a proximal luer connector, the locking clip also covers the luer connector and prevents balloon inflation prior to removal, and the method includes removing the locking clip prior to the step of displacing the expansion catheter distally and displacing the expansion catheter distally prior to inflating the balloon.

In one embodiment, the safety member comprises a safety guard having a stationary part that snaps onto a proximal end of the handpiece and a movable part that forms the proximal end of the balloon catheter and has the luer connector. An elongated arm on the stationary part terminates in a luer guard that receives the luer connector in the retracted position of the balloon catheter and prevents coupling of a mating luer connector of a fluid source thereto. Accordingly, distal movement of the balloon catheter and movable part exposes the luer connector to permit coupling of a mating luer connector, and the method includes advancing the balloon catheter and movable part prior to inflating the balloon.

The native valve leaflets may be removed before delivering the prosthetic valve. Alternatively, the native leaflets may be left in place to reduce surgery time and to provide a stable base for fixing the anchoring skirt within the native valve. In one advantage of this method, the native leaflets recoil inward to enhance the fixation of the metallic anchoring skirt in the body channel. When the native leaflets are left in place, a balloon or other expansion member may be used to push the valve leaflets out of the way and thereby dilate the native valve before implantation of the anchoring skirt. The native annulus may be dilated between 1.0-5 mm from their initial orifice size to accommodate a larger sized prosthetic valve.

In accordance with a preferred aspect, a heart valve includes a prosthetic valve defining therein a non-expandable, non-collapsible orifice, and an expandable anchoring skirt extending from an inflow end thereof. The anchoring skirt has a contracted state for delivery to an implant position and an expanded state configured for outward connection to the surrounding annulus. Desirably, the anchoring skirt is plastically expandable.

In one embodiment, the heart valve comprises a commercially available prosthetic valve having a sewing ring, and the anchoring skirt attaches to the sewing ring. The contracted state of the anchoring skirt may be conical, tapering inward from the first end toward the second end, while in the expanded state the frame is conical but tapering outward from the first end toward the second end. The anchoring skirt preferably comprises a plurality of radially expandable struts at least some of which are arranged in rows. The sewing ring may comprise a solid yet compressible material that is relatively stiff so as to provide a seal against the annulus and has a concave inflow shape that conforms to the annulus.

One method of the application involves increasing the orifice size of the heart valve annulus by 1.0-5.0 mm by plastically expanding the frame. In one embodiment, the prosthetic valve of the valve component is selected to have an orifice size that matches the increased orifice size of the heart valve annulus.

One embodiment of the method further includes mounting the heart valve on a holder having a proximal hub and lumen therethrough. The holder mounts on the distal end of a handle shaft having a lumen therethrough, and the method includes passing a balloon catheter through the lumen of the handle shaft and the holder and within the heart valve, and inflating a balloon on the balloon catheter to expand the anchoring skirt. The heart valve mounted on the holder may be packaged separately from the handle shaft and the balloon catheter. The delivery system including the valve holder is designed to position the balloon within the heart valve so that it inflates within the anchoring skirt, and not within the actual valve components. A safety member is displaced from engagement between a proximal portion of the balloon catheter and a proximal end of the handle shaft, the safety member preventing distal movement of the balloon catheter relative to the handle shaft prior to displacement.

Preferably, a valve delivery system includes an integrated balloon catheter and tubular handle shaft through which the catheter extends. A distal end of the handle shaft includes an adapter which mates with a holder of the heart valve, and a locking sleeve for rapidly connecting the delivery system to the heart valve holder. A balloon of the balloon catheter resides within the adapter and may be advanced distally into position for expanding the anchoring skirt. A tubular balloon introducer sleeve attached when removing the heart valve from a storage jar facilitates passage of the balloon through the heart valve.

A further understanding of the nature and advantages of the present invention are set forth in the following description and claims, particularly when considered in conjunction with the accompanying drawings in which like parts bear like reference numerals.

BRIEF DESCRIPTION OF THE DRAWINGS

The invention will now be explained and other advantages and features will appear with reference to the accompanying schematic drawings wherein:

FIG. 1A is a perspective cutaway view of an aortic annulus showing a portion of the adjacent left ventricle below the ascending aorta, illustrating an exemplary surgical heart valve mounted on a distal section of a delivery handle advancing into position within the aortic annulus along the guide sutures;

FIG. 1B is a view similar to FIG. 1A illustrating the heart valve in a desired implant position at the aortic annulus, and during placement of suture snares;

FIG. 2A is an enlarged view of the aortic valve implant site showing the balloon of the balloon catheter inflated to expand the anchoring skirt, while FIG. 2B shows the balloon deflated and stretched;

FIGS. 3 and 3A are elevational and broken longitudinal sectional views, respectively, of the heart valve delivery system with a balloon catheter in a retracted position;

FIGS. 4 and 4A are elevational and broken longitudinal sectional views, respectively, of the heart valve delivery system with the balloon catheter in an extended position;

FIG. 5A is a partial sectional view of the heart valve delivery system having the prosthetic heart valve and valve holder thereon and in the balloon advanced configuration of FIG. 4A;

FIG. 5B is a partial sectional view similar to FIG. 5A and showing movement of a balloon extension wire to compress a spring upon balloon inflation;

FIG. 5C is similar to FIG. 5A and shows return movement of the balloon extension wire and spring upon balloon deflation;

FIG. 6 is a perspective view of the proximal end of the exemplary heart valve delivery system of the present application showing a locking clip exploded therefrom, while

FIGS. 8A-8C are views of an alternative embodiment for preventing premature deployment of the balloon catheter in the valve delivery system using a toggle lever;

FIGS. 9-12C schematically illustrate alternative valve systems for fluid used to inflate the balloon on the catheter disclosed herein that prevent premature deployment of the balloon;

FIGS. 15A-15C illustrate a sequence of operation of the heart valve delivery system having the safety clip of FIG. 13 thereon, while FIGS. 16A-16C show the same sequence in longitudinal cross-section;

FIGS. 17A and 17B are perspective views of a still further safety guard of the present application showing a toggle lever in two different positions;

FIGS. 18A-18E are side elevational views of a proximal end of an exemplary heart valve delivery system having the safety guard of FIG. 17A attached thereto and showing a sequence of operation;

FIGS. 19A and 19B are enlarged sectional views through a portion of the safety guard and heart valve delivery system illustrating relative engagement and disengagement thereof;

FIGS. 21A-21E are side elevational and enlarged sectional views of the safety guard of FIG. 20A attached to the heart valve delivery system and showing operation thereof;

FIGS. 24A-24C are side elevational views of an exemplary heart valve delivery system and expandable/collapsible prosthetic valve, showing a sequence of deployment thereof.

DETAILED DESCRIPTION OF THE PREFERRED EMBODIMENTS

Figure 6:
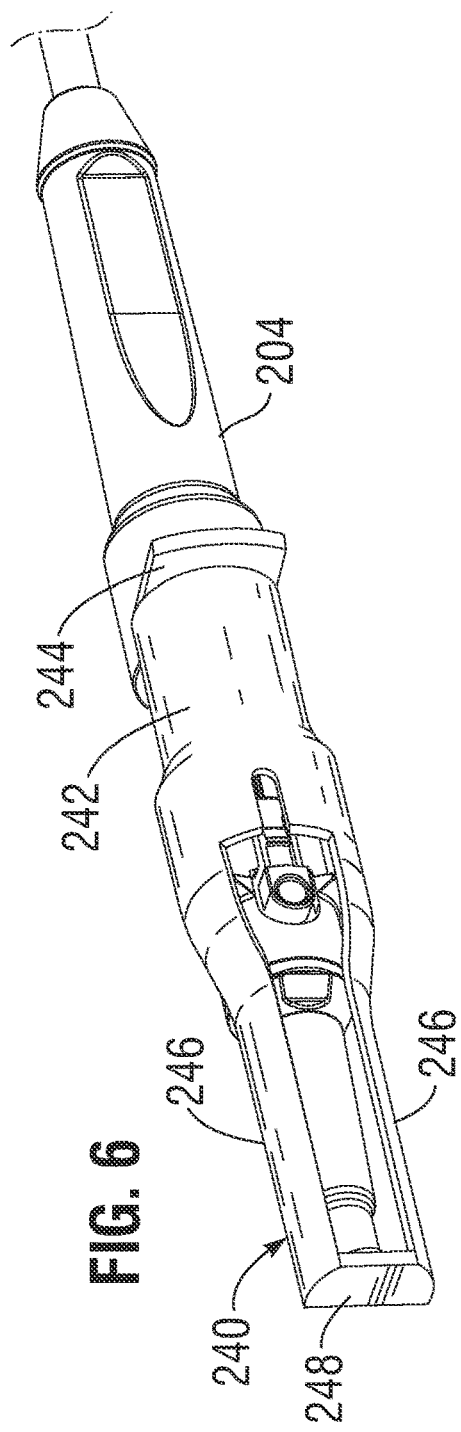

The present invention attempts to overcome drawbacks associated with conventional, open-heart surgery, while also adopting some of the techniques of newer technologies which decrease the duration of the treatment procedure. The prosthetic heart valves of the present invention are primarily intended to be delivered and implanted using conventional surgical techniques, including the aforementioned open-heart surgery. There are a number of approaches in such surgeries, all of which result in the formation of a direct access pathway to the particular heart valve annulus. For clarification, a direct access pathway is one that permits direct (i.e., naked eye) visualization of the heart valve annulus. In addition, it will be recognized that embodiments of the prosthetic heart valves described herein may also be configured for delivery using percutaneous approaches, and those minimally-invasive surgical approaches that require remote implantation of the valve using indirect visualization. However, the latter two approaches—percutaneous and minimally-invasive—invariably rely on collapsible/expandable valve constructs. And, while certain aspects described herein are useful for such valves and techniques, the primary focus and main advantages of the present application is in the realm of non-expandable "surgical" valves introduced in conventional manners.

As described herein, a "unitary" prosthetic heart valve includes a tissue anchor connected to a surgical valve member resulting in certain advantages. The unitary prosthetic heart valve disclosed herein is a hybrid valve member, if you will, with both non-expandable and expandable portions. By utilizing an expandable anchoring skirt or stent coupled to a non-expandable valve member, the duration of the anchoring operation is greatly reduced as compared with a conventional sewing procedure utilizing an array of sutures for a surgical valve. The expandable anchoring skirt may simply be radially expanded outward into contact with the implantation site, or may be provided with additional anchoring means, such as barbs. As stated, conventional open-heart approach and cardiopulmonary bypass familiar to cardiac surgeons are used. However, due to the expandable anchoring skirt, the time on bypass is greatly reduced by the relative speed of implant in contrast to the previous time-consuming knot-tying process.

For definitional purposes, the terms "stent" or "coupling stent" refer to a structural component that is capable of anchoring to tissue of a heart valve annulus. The coupling stents described herein are most typically tubular stents, or stents having varying shapes or diameters. A stent is normally formed of a biocompatible metal frame, such as stainless steel or Nitinol. More preferably, in the context of the present invention the stents are made from laser-cut tubing of a plastically-expandable metal. Other coupling stents that could be used with valves of the present invention include rigid rings, spirally-wound tubes, and other such tubes that fit tightly within a valve annulus and define an orifice therethrough for the passage of blood. It is entirely conceivable, however, that the coupling stent could be separate clamps or hooks that do not define a continuous periphery. Although such devices sacrifice some contact uniformity, and speed and ease of deployment, they could be configured to work in conjunction with a particular valve member.

A distinction between self-expanding and balloon-expanding stents exists in the field. A self-expanding stent may be crimped or otherwise compressed into a small tube and possesses sufficient elasticity to spring outward by itself when a restraint such as an outer sheath is removed. In contrast, a balloon-expanding stent is made of a material that is substantially less elastic, and indeed must be plastically expanded from the inside out when converting from a contracted to an expanded diameter. It should be understood that the term balloon-expanding stents encompasses plastically-expandable stents, whether or not a balloon is used to actually expand it (e.g., a device with mechanical fingers could expand the stent). The material of the stent plastically deforms after application of a deformation force such as an inflating balloon or expanding mechanical fingers. Consequently, the term "balloon-expandable stent" should be understood as referring to the material or type of the stent as opposed to the specific expansion means.

The term "valve member" refers to that component of a heart valve that possesses the fluid occluding surfaces to prevent blood flow in one direction while permitting it in another. As mentioned above, various constructions of valve members are available, including those with flexible leaflets and those with rigid leaflets, or even a ball and cage arrangement. The leaflets may be bioprosthetic, synthetic, metallic, or other suitable expedients. In a preferred embodiment, the non-expandable valve member is an "off-the-shelf" standard surgical valve of the type that has been successfully implanted using sutures for many years, such as the Carpentier-Edwards PERIMOUNT Magna® Aortic Heart Valve available from Edwards Lifesciences of Irvine, Calif., though the autonomous nature of the valve member is not absolutely required. In this sense, a "off-the-shelf" prosthetic heart valve is suitable for stand-alone sale and use, typically including a non-expandable, non-collapsible support structure having a sewing ring capable of being implanted using sutures through the sewing ring in an open-heart, surgical procedure.

Desirably, the present application includes delivery systems for a prosthetic heart valve having a single stage implantation in which a surgeon secures a hybrid valve having an anchoring skirt and valve member to a valve annulus as one unit or piece (e.g., a "unitary" valve). Certain features of the hybrid anchoring skirt and valve member are described in U.S. Pat. No. 8,308,798, filed Dec. 10, 2009, as well as in U.S. Patent Publication No. 2012/0065729, filed Jun. 23, 2011, the contents of which are expressly incorporated herein. It should be noted that "two-stage" prosthetic valve delivery disclosed in the aforementioned publication refers to the two primary steps of a) anchoring structure to the annulus, and then b) connecting a valve member, which does not necessarily limit the valve to just two parts. Likewise, the valve described herein is especially beneficial in a single stage implant procedure, but that does not necessarily limit the overall system to just one part. For instance, the heart valve disclosed herein could also use an expanding base stent which is then reinforced by the subsequently implanted heart valve. Because the heart valve has a non-expandable and non-collapsible annular support structure, and a plastically-expandable anchoring skirt, it effectively resists recoil of a self-expanded base stent.

As a point of further definition, the term "expandable" is used herein to refer to a component of the heart valve capable of expanding from a first, delivery diameter to a second, implantation diameter. An expandable structure, therefore, does not mean one that might undergo slight expansion from a rise in temperature, or other such incidental cause such as fluid dynamics acting on leaflets or commissures. Conversely, "non-expandable" should not be interpreted to mean completely rigid or a dimensionally stable, as some slight expansion of conventional "non-expandable" heart valves, for example, may be observed.

In the description that follows, the term "body channel" is used to define a blood conduit or vessel within the body. Of course, the particular application of the prosthetic heart valve determines the body channel at issue. An aortic valve replacement, for example, would be implanted in, or adjacent to, the aortic annulus. Likewise, a mitral valve replacement will be implanted at the mitral annulus. Certain features of the present invention are particularly advantageous for one implantation site or the other, in particular the aortic annulus. However, unless the combination is structurally impossible, or excluded by claim language, any of the heart valve embodiments described herein could be implanted in any body channel.

A "quick-connect" aortic valve bio-prosthesis described herein is a surgically-implanted medical device for the treatment of aortic valve stenosis. The exemplary quick-connect device comprises an implantable bio-prosthesis and a delivery system for its deployment. The device, delivery system and method of use take advantage of the proven hemodynamic performance and durability of existing commercially available, non-expandable prosthetic heart valves, while improving ease of use and reducing total procedure time. This is mainly accomplished by eliminating the need to suture the bio-prosthesis onto the native annulus as is currently done per standard surgical practice, and typically requires 12-24 manually-tied sutures around the valve perimeter. Also, the technique may obviate the need to excise the leaflets of the calcified valve and debride or smooth the valve annulus.

An exemplary hybrid prosthetic heart valve and valve holder is disclosed in U.S. Patent Publication No. 2012/0065729 to Pintor, et al., filed Jun. 23, 2011, to which priority is claimed, and which is hereby expressly incorporated by reference herein. For a more detailed description of the heart valve, reference is made to FIGS. 5-15 of the Pintor publication.

As seen in FIGS. 1A-1B and 2A-2B, a prosthetic heart valve 20 is assembled on a valve holder 22. The heart valve 20 desirably includes a valve member 24 having an anchoring skirt 26 attached to an inflow end thereof, such as to a sewing ring 28. The valve member 24 is desirably non-collapsible and non-expandable, while the anchoring skirt 26 may expand from the contracted state shown into an expanded state, as will be described. In one embodiment, the valve member 24 comprises a Carpentier-Edwards PERIMOUNT Magna® Aortic Heart Valve available from Edwards Lifesciences of Irvine, Calif., while the anchoring skirt 26 includes an inner plastically-expandable frame or stent covered with fabric.

As seen in FIG. 2B (and in more detail in FIGS. 6-8 of the Pintor publication), the valve holder 22 preferably includes a central tubular hub portion 30 having internal threads, and a plurality of stabilizing legs 32 projecting axially and radially outward therefrom. Each of the three stabilizing legs 32 contacts and attaches to a cusp portion of the valve member 24 between commissure posts 36. An upper end of the hub portion 30 also has an internal star-shaped bore that provides a valve-size-specific keyed engagement with a delivery system. The valve holder 22 secures with sutures to the valve member 24 from the time of manufacture to the time of implant, and is stored with the valve member.

In one embodiment, the holder 22 is formed of a rigid polymer such as Delrin polypropylene that is transparent to increase visibility of an implant procedure. The holder 22 provides relatively wide openings between the stabilizing legs 32 to provide a surgeon good visibility of the valve leaflets, and the transparency of the legs further facilitates visibility and permits transmission of light therethrough to minimize shadows.

The completed valve member 24 provides the occluding surfaces for the prosthetic heart valve 20, preferably in the form of flexible bioprosthetic leaflets. For example, the valve leaflets may be taken from another human heart (cadaver), a cow (bovine), a pig (porcine valve) or a horse (equine). Alternatively, the valve member may comprise mechanical components rather than biological tissue. Although an autonomous (i.e., capable of stand-alone surgical implant) flexible leaflet valve member 24 is described and illustrated, alternative valve members that have rigid leaflets, or are not fully autonomous may be substituted.

For bioprosthetic valves, an exemplary process includes storing the prosthetic heart valve 20 in a preservative solution after manufacture and prior to use. A preservative such as glutaraldehyde is provided within a storage jar. This "wet" storage arrangement applies to the illustrated heart valve 20 shown, which includes conventional bioprosthetic leaflets, but could also be used without a preservative solution for bioprosthetic leaflets that have been dried and also for mechanical valves.

The general function of the anchoring skirt 26 is to provide the means to attach the prosthetic valve member 24 to the native aortic root. This attachment method is intended as an alternative to the present standard surgical method of suturing aortic valve bio-prostheses to the aortic valve annulus, and is accomplished in much less time. Further, this attachment method improves ease of use by eliminating most of not all suturing. The anchoring skirt 26 may be a pre-crimped, tapered, 316L stainless steel balloon-expandable stent, desirably covered by a polyester fabric to help seal against paravalvular leakage and promote tissue ingrowth once implanted within the annulus. The anchoring skirt 26 transitions between the tapered constricted shape of FIGS. 1A-1B to its flared expanded shape shown in FIGS. 2A-2B.

An exemplary implant procedure for the prosthetic heart valve 20 was disclosed with reference to FIGS. 16A-16J of the Pintor publication, a portion of which is shown in the present application in FIGS. 1A-1B and 2A-2B. These figures are sectional views through an isolated aortic annulus showing a portion of the adjacent left ventricle and ascending aorta with sinus cavities. The two coronary arteries are also shown. As will be explained, the anchoring skirt 26 is deployed against the native leaflets or, if the leaflets are excised, against the debrided aortic annulus as shown.

In the ensuing procedure drawings, the heart valve 20 is oriented with an inflow end down and an outflow end up. That is, blood flow through the valve 20 is upward as shown in the drawings. Therefore, the terms inflow side and down may be used interchangeably at times, as well as the terms outflow side and up. Furthermore, the terms proximal and distal are defined from the perspective of the surgeon delivering the valve inflow end first, and thus proximal is synonymous with up or the outflow side, and distal with down or the inflow side.

An implant procedure involves delivering the heart valve 20 and expanding the anchoring skirt 26 at the aortic annulus. Because the valve member 24 is non-expandable, the entire procedure is typically done using the conventional open-heart technique. However, because the anchoring skirt 26 is implanted by simple expansion, with reduced suturing, the entire operation takes less time. This hybrid approach will also be much more comfortable to surgeons familiar with the open-heart procedures and commercially available heart valves.

A preliminary step in preparing an aortic annulus for receiving the heart valve includes installation of guide sutures 38. The aortic annulus is shown schematically isolated and it should be understood that various anatomical structures are not shown for clarity. The annulus includes a fibrous ring of tissue that projects inward from surrounding heart walls. The annulus defines an orifice between the ascending aorta and the left ventricle. Although not shown, native leaflets project inward at the annulus to form a one-way valve at the orifice. The leaflets may be removed prior to the procedure, or left in place as mentioned above. If the leaflets are removed, some of the calcified annulus may also be removed, such as with a rongeur. The ascending aorta commences at the annulus with three outward bulges or sinuses, two of which are centered at coronary ostia (openings) leading to coronary arteries. As will be seen below, it is important to orient the prosthetic valve member 24 so that its commissure posts 36 are not aligned with and thus not blocking the coronary ostia.

The surgeon attaches the guide sutures 38 at three evenly spaced locations around the aortic annulus. In the illustrated embodiment, the guide sutures 38 attach to locations below or corresponding to the coronary ostia (that is, two guide sutures are aligned with the ostia, and the third centered below the non-coronary sinus). The guide sutures 38 are preferably looped twice through the annulus from the outflow or ascending aorta side to the inflow or ventricular side. Of course, other suturing methods or pledgets may be used depending on surgeon preference.

FIG. 1A shows the heart valve 20 on the distal end of a delivery system 110 and at a desired implant position at the aortic annulus, and during placement of tubular suture snares. The sewing ring 28 is positioned supra-annularly, or above the narrowest point of the aortic annulus, so as to allow selection of a larger orifice size than a valve placed intra-annularly. A dilatation balloon 112 on the distal end of a balloon catheter 114 of the delivery system 110 can be seen just beyond the distal end of the anchoring skirt 26.

The surgeon delivers a plurality of suture snares 120 down each free length of the guide sutures 38 into contact with the upper or outflow side of the sewing ring 28. The snares 120 enable downward pressure to be applied to the ring 28 and thus the valve 20 during the implant procedure, which helps insure good seating of the ring 28 on the annulus. The snares 120 also provide rigid enclosures around each of the flexible guide sutures 38 which helps avoid entanglement with other moving surgical instruments, as will be appreciated. As there are three pairs of guide sutures 38 (six free lengths) three snares 120 are utilized, though more or less is possible. The snares 120 are typically tubular straw-like members of medical grade plastic.

FIG. 1A shows all of the pairs of suture snares 120 bent outward and a majority of the delivery system 110. The delivery system 110 is in a configuration prior to advancement of the balloon catheter 114 and its dilatation balloon 112.

FIG. 1B shows the delivery system after advancement of the balloon catheter 114 and dilatation balloon 112 relative to a handpiece 204 on a proximal end of an elongated handle shaft 130. Although it will be described in greater detail below with respect to FIGS. 3-5, the handle shaft 130 terminates in a valve holder adapter 208 that directly connects to the holder 22. The handle shaft 130 is desirably malleable for manipulating the orientation of the heart valve 20 during delivery through the ascending aorta.

After distal advancement, the balloon 112 projects downward through the valve 20, and into the left ventricle. As will be explained below, the delivery system 110 provides binary position displacement of the balloon 112, either retracted substantially within the prosthetic heart valve 20 or advanced precisely as far as necessary to expand the anchoring skirt 26 of the valve.

FIG. 2A shows the dilatation balloon 112 inflated to expand the anchoring skirt 26 against the ventricular side of the aortic annulus. The balloon 112 desirably has a frusto-conical profile that expands the anchoring skirt 26 into a frustoconical expanded state. Not only does this conform better to the subannular contours but over expands somewhat the annulus such that a larger valve maybe utilized than without the expansion. One advantage of using a plastically-expandable stent is the ability to expand the native annulus to receive a larger valve size than would otherwise be possible with conventional surgery. Desirably, the left ventricular outflow tract (LVOT) is significantly expanded by at least 10%, or for example by 1-5 mm, and the surgeon can select a heart valve 20 with a larger orifice diameter relative to an unexpanded annulus. Even a 1 mm increase in annulus size is significant since the gradient is considered to be proportional to the radius raised to the $4^{th}$ power.

Simple interference between the anchoring skirt 26 and the annulus may be sufficient to anchor the heart valve 20, or interacting features such as projections, hooks, barbs, fabric, etc. may be utilized. For example, a distal end of the anchoring skirt may expand more than the rest of the anchoring skirt so that peaks in the strut row farthest from the prosthetic valve project outward into the surrounding annulus. Also, the balloon 112 may have a larger distal expanded end than its proximal expanded end so as to apply more force to the free end of the anchoring skirt 26 than to the prosthetic valve member 24. In this way, the prosthetic valve member 24 and flexible leaflets therein are not subject to high expansion forces from the balloon 112.

The balloon 112 desirably is tapered to have an angle between about 0-45°, and more preferably is about 38° (0° being a cylindrical expansion). Alternatively, the balloon 112 may include curves or non-axi-symmetric contours to deform the anchoring skirt 26 to various desired shapes to fit better within the particular annulus. Indeed, various potential shapes are described in U.S. Patent Publication 2008/0021546, entitled System for Deploying Balloon-Expandable Heart Valves, published Jan. 24, 2008, the disclosure of which is expressly incorporated herein.

FIG. 2B then illustrates the balloon 112 deflated and contracted. A spring mechanism within the delivery system 110 along with longitudinal pleats in the balloon 112 facilitate contraction of the balloon when deflated into an extremely narrow configuration which makes removal easier.

The next step is retraction of the balloon 112 and entire delivery system 110 from the valve holder 22 before or after removal of the snares 120, which happens only as a contingency. Although not shown, the most common procedure after expansion of the balloon 112 and skirt 26 involves the surgeon severing the connecting sutures between the valve holder 22 and the prosthetic valve member 24, and removing the entire delivery system. Severing a middle length of each suture that connects the holder 22 to the valve member 24 permits the delivery system 110 with the holder at the distal end to be pulled free from the valve 20. However, the delivery system 110 also features a simple engagement and detachment mechanism explained below that enables the surgeon to easily remove the system 110 from the holder 22 which remains attached to the valve 20. This detachment may be needed to replace the balloon catheter, such as if the original balloon develops a leak or for some reason does not deploy properly. This "quick-release" arrangement permits the surgeon to rapidly exchange catheters while leaving the valve 20 in place.

Finally, the prosthetic heart valve 20 is fully implanted with the guide sutures 38 knotted on the proximal face of a sewing ring 28. The guide sutures 38 are primarily for rotationally orienting the heart valve 20 as it seats against the aortic annulus and to define a plane for axial positioning. As such, the guide sutures 38 are not believed strictly necessary for securing the heart valve 20 at the annulus. Moreover, devices other than knots such as clips or cinches could be used to secure the guide sutures 38 speed up the process.

FIGS. 3-3A and 4-4A show the prosthetic heart valve delivery system 110 in elevational and sectional views, in both the retracted and advanced positions of the balloon catheter 114. On its proximal end, the system 110 includes an end cap 190 having a luer connector 192, a balloon extension spring 194, a spring compression pin 196, a balloon displacer 198, an inflation tube 199, and a balloon extension wire 200. The mid-portion of the system 110 includes a centering washer 202, the handpiece 204, and the aforementioned malleable handle shaft 130. Finally, distal components of the system 110 include a tubular locking sleeve 206, the valve holder adapter 208, the dilatation balloon 112, and an insert molded tip 210. The entire system preferably has a length from the proximal end of the luer connector 192 to the balloon wire tip 210 of between about 100 and 500 mm.

FIGS. 3 and 3A show the end cap 190 and balloon displacer 198 joined together, preferably with adhesive or other such coupling means. The assembly of the end cap 190 and balloon displacer 198 forms a handle of the balloon catheter 114 and may be displaced linearly with respect to the handpiece 204. The malleable handle shaft 130 extends distally from the handpiece 204 and is preferably secured thereto with adhesive or the like. The valve holder adapter 208 fixes to a distal end of the handle shaft 130, but the locking sleeve 206 slides over the handle. In this regard, the balloon catheter 114 slides linearly along and within the "introducer" comprising the handpiece 204, handle shaft 130, and valve holder adapter 208, as seen in FIGS. 4 and 4A.

When assembled as seen in FIG. 3A, an elongated lumen (not numbered) extends from the proximal luer connector 192 to the interior of the balloon 112. The luer connector 192 provides an attachment nipple for an inflation system (not shown) for inflation of the balloon 112. The balloon 112 is desirably inflated using controlled, pressurized, sterile physiologic saline. The lumen passes through the end cap 190, balloon displacer 198, and then through the inflation tube 199 which is affixed at one end to the displacer and at another end to a proximal end of the balloon. The balloon displacer 198 thus moves the proximal end of the balloon.

The balloon catheter 114 of the delivery system 110 has two binary longitudinal positions relative to the handpiece 204 and its associated structures. In the retracted position shown in FIGS. 3 and 3A, the connected end cap 190, balloon displacer 198, inflation tube 199, and balloon 112 are retracted to the left with respect to the handpiece 204. Note the spacing A between a distal shoulder 230 of the balloon displacer 198 and the centering washer 202 within the handpiece 204. The balloon 112 resides partway within the holder adapter 208 in this position. Once the balloon catheter is displaced to the right, as seen in FIGS. 4 and 4A, the spacing A disappears and the balloon 112 projects out from within the handle adapter 208.

The delivery system 110 provides an extremely accurate system for positioning the balloon 112 relative to the heart valve, and in particular the anchoring skirt 26. Because of the simple engagement between the handle adapter 208 and the handle shaft 130, very little tolerance errors are introduced. The handle adapter 208 is fixed to the elongated handle shaft 130, which in turn is fixed to the handpiece 204. Movement of the balloon catheter 114 relative to the handpiece 204 thus displaces the balloon 112 in a 1:1 correspondence with respect to the holder 22 and attached heart valve 20. Furthermore, a pair of small resilient détentes 232 provided on the balloon displacer 198 engage similarly sized cutouts 234 on the proximal end of the handpiece 204. This locks the position of the balloon catheter 114 with respect to the handpiece 204, or in other words locks the position of the balloon 112 with respect to the anchoring skirt 26.

One aspect of the present application is the integration of a balloon catheter within the delivery system 110. Namely, previous systems for delivering prosthetic heart valves in this manner have included separate introducer and balloon catheter elements, where the balloon catheter inserts through the tubular introducer. Although such a system may work suitably for its intended purpose, an integrated balloon catheter 114 within the delivery system 110 provides distinct advantages. First of all, if there is a problem with the balloon, such as a puncture, the surgeon need not retract the entire balloon catheter 114 through the introducer and replace it with another one, which is time consuming. Instead, the delivery system 110 is merely decoupled from the valve holder 22, and a replacement delivery system 110 including a new balloon catheter 114 engaged to the holder. Secondly, and perhaps more evident, a single delivery system 110 replacing multiple parts speeds up the entire process and facilitate ease-of-use. The surgeon no longer has to couple multiple parts together prior to attaching to the heart valve holder, or manipulate a separate balloon catheter relative to an introducer tube. Sliding a balloon catheter through an elongated introducer opens up the risk of snags and balloon tears. Finally, the amount of packaging is reduced accordingly.

FIGS. 5A-5C illustrate a preferred configuration for coupling the delivery system 110 to the prosthetic heart valve 20 and holder 22 assembly. In particular, a tubular balloon introducer sleeve 212 threads within the holder 22. Preferably, the user couples the introducer sleeve 212 to the holder 22 at the time of preparing the valve 20 for surgery, and more preferably the sleeve 212 may be used to extract the valve 20 from its storage jar. A portion of the sleeve 212 projects in a proximal direction from within the holder 22 and presents a tubular entryway for the balloon wire tip 210 and balloon 112. The user inserts the delivery system 110 through the introducer sleeve 212 until the valve holder adapter 208 contacts the holder 22.

With reference to FIGS. 3A and 5A, the valve holder adapter 208 includes an elongated through bore 214 which receives the proximal end of the introducer sleeve 212. Although not shown, a plurality of cantilevered fingers extend longitudinally along the adapter 208 terminating at its distal end. Each of the fingers includes an inwardly directed bump 218 (FIG. 5A). Sliding the adapter 208 over the introducer sleeve 212 such that the distal end contacts a proximal end of the holder 22 brings the bumps 218 over an external groove (not numbered) on the exterior of the sleeve 212 so as to provide an interference connection. The locking sleeve 206 then slides over the holder adapter 208, as seen in FIG. 5A. Because the inner bore of the locking sleeve 206 fits closely around the adapter 208, the cantilevered fingers are retained in their aligned orientation with the bumps 218 in the groove of the sleeve 212. The locking sleeve 206 desirably frictionally engages the exterior of the adapter 208 to prevent two parts from easily coming apart. Alternatively, a separate detente or latch may be provided for more security. Ultimately, when the locking sleeve 206 is in the position of FIG. 5A, the delivery system 110 is securely coupled to the valve holder 22. Moreover, the balloon 112 extends through the balloon introducer sleeve 212 to be positioned within the expandable skirt 26.

Another advantageous feature of the present application is a keyed engagement between delivery systems 110 and holders 22 for the same size of heart valves. In particular, the hub portion 30 of the holder 22 has an internal star-shaped bore (not shown) which is sized and patterned to be keyed to an external star-shaped rim 220 provided on the holder adapter 208 (see FIG. 4). Because the balloon catheter 114 is integrated with the delivery system 110, and each balloon catheter is sized for a particular valve, only the delivery system 110 which is designed for that particular valve should be coupled to its holder. That is, each expansion skirt 26 must be expanded to a particular diameter, which requires different sizes of balloons 112. Consequently, each differently sized valve holder and a delivery system combination has a unique star-shaped pattern which prevents mating with a different size.

Typically, the delivery system 110 is packaged separately from the heart valve 20 and holder 22, and this keying arrangement prevents misuse of the wrong delivery system. Additionally, if the balloon breaks and another delivery system must be rapidly obtained and utilized, the keying arrangement prevents the wrong delivery system from being substituted. There are typically 6-8 valve sizes in 2 millimeter increments, and thus a similar number of unique keyed couplings will be provided. Furthermore, the star-shaped pattern disclosed permits engagement at a plurality of rotational orientations. In a preferred embodiment, the user must rotate the delivery system 110 no more than 30° before the star-shaped rim 220 of the adapter 208 mates with the internal star-shaped bore of the holder 22. This is extremely beneficial if changing out the delivery system 110, because the original elongated handle shaft 130 may be bent into a particular orientation which is much easier to replicate if the keyed features do not have to be oriented in only one or two angular relations.

As mentioned, the elongated handle shaft 130 is malleable or bendable into various shapes. This bendability of the handle shaft 130 significantly enhances the ability of a surgeon to correctly position the heart valve 20 as it advances toward the annulus. Often, access passageways into the heart during a surgical procedure are somewhat confined, and may not provide a linear approach to the annulus. Accordingly, the surgeon bends the handle shaft 130 to suit the particular surgery. Various materials and constructions may be utilized to provide a malleable tube for use as the handle shaft 130. The handle shaft 130 must be axially rigid so that the user can position the heart valve in the annulus with confidence. In a preferred embodiment, an aluminum tube having a chromate (e.g., Iridite) coating is used. Aluminum is particularly well-suited for forming small tubes that can be bent without kinking, but should be coated with Iridite or the like to prevent deterioration in and reaction with the body.

The balloon inflation tube 199 and balloon extension wire 200 are formed of materials that have column strength but are relatively flexible in bending. As explained further below, the wire may be Nitinol while the inflation tube 199 is desirably formed of a braid reinforced thermoplastic elastomer (TPE) such as a polyether block amide known under the trade name of PEBAX® (Arkema of Colombes, France).

As the delivery system 110 may be subjected to several bends in use, care must be taken to ensure that the concentric tubes and wire do not introduce misalignment. That is, smaller diameter objects tend to travel shorter paths within larger concentric tubes, thus cause them to extend out of the distal end of the tubes after being bent. As such, the balloon inflation tube 199 is desirably closely sized to match the inner diameter of the malleable handle shaft 130. This close matching of tube sizes ensures that the axial position of the balloon 112, which is affixed to the end of the balloon inflation tube 199, does not shift much relative to the axial position of the prosthetic heart valve 20, which is affixed relative to the end of the malleable handle shaft 130. The balloon extension wire 200 has a size relative to the ID of the balloon inflation tube 199 sufficient to permit good flow of saline when filling the balloon 112.

The present application also provides an improved balloon 112 and system for deploying and removing it. As seen in the deflated views, the balloon 112 preferably comprises a plurality of longitudinal pleats which help reduce its radial configuration for passage through the delivery system 110. Furthermore, the balloon extension wire 200 extends through the balloon inflation tube 199, through the dilatation balloon 112, and terminates in a molded balloon wire tip 210 affixed to the distal end of the balloon. The path of the wire 200 is seen in the sectional views of FIGS. 3A and 4A. Although the proximal end of the balloon 112 fastens to the inflation tube 199, and thus from there to the handpiece 204, the distal tip 210 does not. Instead, the wire 200 fastens to the spring compression pin 196 which translates within a lumen in the proximal end cap 190, and engages the balloon extension spring 194 therein. In this regard, the balloon extension wire 200 moves independently within the delivery system 110 instead of being fixedly attached. This, in turn, allows the distal end of the balloon 112 to move with respect to the proximal end. This arrangement is seen best in FIGS. 5A-5C.

The exemplary delivery system balloon 112 has a relatively high diameter-to-length ratio compared to other surgical balloons, such as those used to expand cardiovascular stents. This makes it particularly difficult for the balloon 112 to return to a small geometry upon deflation after deployment. Balloons of such size ratios tend to "butterfly" by forming wings that prevent removal through the valve holder without the application of high forces, which may cause damage to the valve itself. The exemplary delivery system 110 and balloon 112 include several advances from earlier heart valve delivery systems that facilitate atraumatic removal of the balloon 112. First, as mentioned above, a series of longitudinal pleats are heat set into the wall of the balloon 112 to facilitate self-collapse during deflation. Further, the distal end of the balloon 112 moves relative to the proximal end to enable lengthening of the balloon during deflation. This lengthening occurs automatically by virtue of the wire 200 which is spring-biased to stretch the balloon longitudinally. It should be noted that easy deflation and removal of the balloon 112 permits rapid replacement of the balloon catheter in case of a problem, such as insufficient inflation.

FIG. 5A is a sectional view with the balloon 112 advanced as in FIG. 4A. In this configuration, the spring 194 has a length of $x_1$, and the spring compression pin 196 is all the way to the right within the end cap cavity. In this "resting" state with the balloon 112 deflated, the spring 194 may be relaxed or under a slight compressive preload. Subsequently, saline is introduced via the proximal luer connector 192 and travels distally along the length of the balloon catheter components to inflate the balloon 112. Inflation of the balloon 112 causes radial expansion but axial foreshortening, thus displacing the distal tip 210 to the left as shown in FIG. 5B. This, in turn, displaces the balloon extension wire 200 and attached spring compression pin 196 to the left against the resiliency of the spring 194. Ultimately, the spring is compressed to a second shorter length $x_2$. In a preferred embodiment, the spring 194 undergoes complete compression to its solid length so as to provide a positive stop on proximal movement of the wire 200 and attached balloon distal tip 210. This helps ensure proper expansion of the anchoring skirt 26, as will be more fully explained. The proximal movement of the distal tip 210 against the reaction force of the spring 194 places the wire 200 in compression.

Finally, FIG. 5C illustrates deflation of the balloon 112 by pulling a vacuum through the inflation movement and return movement to the right of the distal tip 210 and balloon extension wire 200. This movement is encouraged, and indeed forced, by expansion of the spring 194. The force of the spring 194 is calibrated so as to elongate the pleated balloon 112 so it assumes its previous radially constricted diameter, or as close as possible to it. Furthermore, the wire 200 may be rotated about its axis to further encourage constriction of the balloon 112 by causing the pleats to further fold in a helical fashion. This can be accomplished by extending a portion of the wire 200 from the proximal end of the Luer connector 192 so as to be grasped and rotated by forceps, or otherwise providing a lever or thumb plunger (not shown) fastened to the wire and projecting laterally from the system. Still further, the spring compression pin 196 may be constrained to translate within a helical track. In the latter case, the pin 196 may include a bayonet-type mount that locks within detents in both ends of the helical track. The spring-biased lengthening and consequent radial contraction of the balloon 112 facilitates its proximal removal through the now-deployed prosthetic heart valve 20.

As mentioned above, the balloon 112 desirably has a frustoconical profile that expands the anchoring skirt 26 into a frusto-conical expanded state. More typically, and as shown in FIG. 5B, the balloon 112 is generally spherical when expanded. Nevertheless, a spherical balloon will outwardly expand the anchoring skirt 26 into a frusto-conical shape due to the connection at one end of the inner stent frame 80 to the heart valve sewing ring 28. To ensure sufficient and proper outward expansion of the anchoring skirt 26, the balloon 112 is axially positioned such that a midline 280 indicated around the maximum circumference (equatorial line) thereof registers with the distalmost end 282 of the skirt. In doing so, the widest part of the balloon 112 corresponds to the end of the skirt 26, which tends to expand the skirt conically. A tolerance of 1-2 mm between the location of the midline 280 and the distalmost end 282 of the skirt is acceptable which may occur for different sizes of valves and associated skirt 26.

FIG. 5A shows an exemplary stepped balloon construction wherein the balloon 112 is desirably offset molded to form the midline 280 as a small step in the balloon wall. That is, the opposed balloon mold halves will have a slightly different diameter, such that a physical step in the final product is formed—the midline 280. Alternatively, the midline 280 may be formed by a small equatorial rib or indent formed in the mold process, or even with an ink marking, though the latter may not be suitable for surgical application. The midline 280 will be visible on the balloon 112 in both its deflated and inflated states, and is extremely useful as a reference line during assembly and quality control of the delivery system 110. For instance, the components of the system 110 are assembled and the location of the balloon 112 in its advanced position is checked against the anchoring skirt 26. Since the balloon 112 foreshortens when it is inflated, the reference midline 280 should be beyond the distalmost end 282 of the skirt 26 when the balloon is deflated, a location that can easily be inspected during assembly.

It should be mentioned that as an alternative to a balloon, a mechanical expander may be used to expand the anchoring skirt 26 shown above. For instance, a mechanical expander may include a plurality of spreadable fingers actuated by a syringe-like apparatus, as seen in U.S. Pat. No. 8,308,798, filed Dec. 10, 2009, incorporated above. The fingers are axially fixed but capable of pivoting or flexing with respect to a barrel. The distal end of a plunger has an outer diameter that is greater than the diameter circumscribed by the inner surfaces of the spreadable fingers, such that distal movement of the plunger with respect to the barrel gradually cams the fingers outward within the coupling stent. Alternatives include mechanical fingers that are not pivotally attached to a handle attachment member. In this way, an inflation balloon causes direct radial expansion of the fingers instead of a pivoting movement. Therefore, the term "expansion catheter" pertains to balloon catheters, purely mechanical spreaders on the end of a catheter, or combinations thereof. Also, "plastically-expandable" encompasses materials that can be substantially deformed by an applied force, such as by a balloon or a mechanical spreader, to assume a different shape. Some self-expanding stents may be deformed to a degree by an applied force beyond their maximum expanded dimension, but the primary cause of the shape change is elastic rebound as opposed to a plastic deformation.

The present delivery system advantageously prevents premature advancement of the balloon catheter (or expander) so that the balloon 112 remains retracted within the confines of the prosthetic heart valve 20 during advancement of the valve into position within the aortic annulus. As will be readily apparent, the surgeon advances the entire delivery system 110 with the heart valve 20 at its distal end through the open chest cavity or port and through the aortic arch and down the ascending aorta into the implant position. Pushing on the proximal end of the delivery system 110 carries the risk of accidentally displacing the balloon catheter 114 relative to the handpiece 204 prior to the desired deployment stage. A protruding balloon 112 may damage the coronary ostia or make insertion difficult by enlarging the device profile. Consequently, the present application contemplates various means for physically preventing movement of the balloon catheter, preferably coupled with a visual reminder not to deploy the catheter prematurely.

Figure 7A:
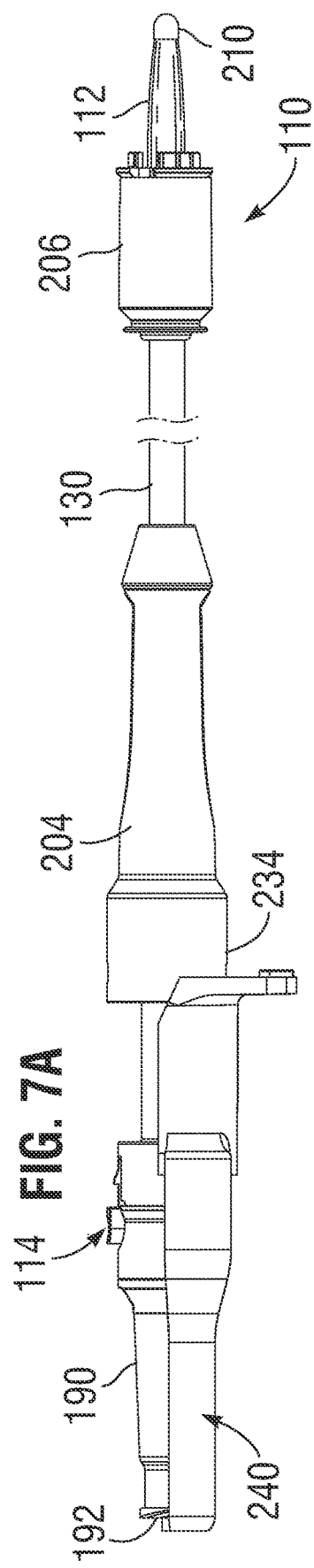
FIGS. 7A and 7B are elevational and broken longitudinal sectional views, respectively, of the heart valve delivery system with a balloon catheter held in the retracted position by the locking clip.
Figure 7B:
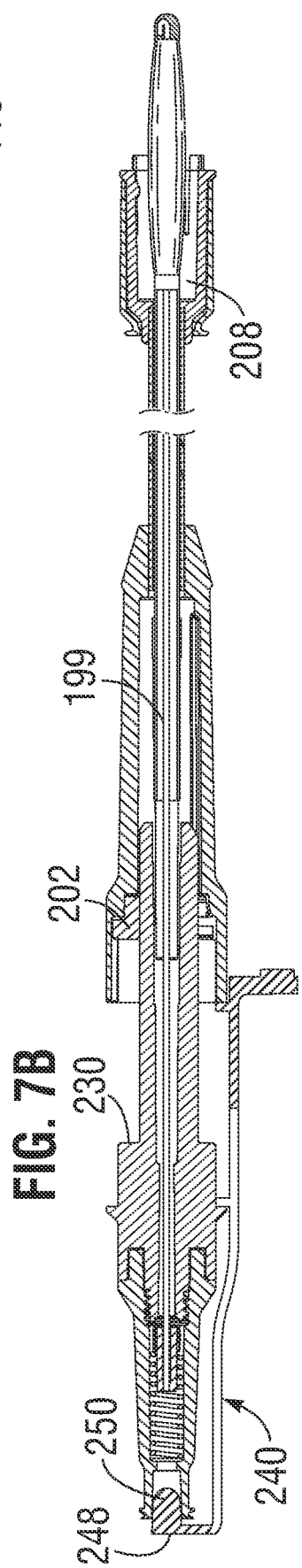

For instance, FIG. 6 is a perspective view of the proximal end of the exemplary heart valve delivery system 110 showing a locking clip 240 attached thereto. As seen in FIGS. 7A and 7B, the locking clip 240 snaps to the exterior of the end cap 190 and handpiece 204 and holds the balloon catheter in a retracted position by presenting a physical barrier to relative movement of those two elements. The locking clip 240 includes a semi-tubular body 242 terminating in a thumb ledge 244 on its distal end. The semi-tubular body 242 has internal features that match the external features on the handpiece 204. Specifically, although not shown, the interior of the semi-tubular body 242 has circumferential ridges that engage the proximal end of the handpiece 204 and both frictionally engage the handpiece and provide an impediment to distal axial movement of the clip 240 relative to the handpiece. The locking clip 240 bifurcates into two elongated rails 246 that extend proximally from the body 242 and come together at a proximal bridge 248 having an inwardly-directed node 250 (FIG. 7B). The node 250 fits closely within the lumen of the luer connector 192 and provides a physical barrier and visual indicator to prevent premature attachment of a balloon inflation source. Further, interior features on the two elongated rails 246 engage matching contours on the balloon catheter end cap 190.

The clip 240 assembles to the delivery system 110 as shown with the balloon catheter in the retracted position (i.e., the position shown in FIG. 3). First the node 250 inserts into the luer connector 192 lumen, and then the clip 240 snaps over the end cap 190 and handpiece 204. The connection between the clip 240 and delivery system 110 is frictional and the clip can easily be removed, but provides a physical barrier and visual reminder to prevent premature distal deployment of the balloon catheter 114, as well as prevents connection of a balloon inflation source. Furthermore, the thumb ledge 244 on the clip 240 provides a convenient ergonomic feature that facilitates one-handed control of the system advancement. After the surgeon advances the system and prosthetic heart valve 20 into position within the aortic annulus, he/she removes the clip 240 to enable deployment of the balloon catheter 114 and connection of an inflation source. The clip 240 is typically plastic and is discarded.

Other possible barriers to premature balloon catheter deployment/balloon inflation are contemplated. In one configuration shown in FIGS. 8A-8C, a toggle lever 260 connects to both the end cap 190 and handpiece 204 and may be displaced in either direction to alternately deploy and retract the balloon catheter. More specifically, the toggle lever 260 includes a thumb piece 262 that projects outward from the delivery system 110, a hinge 264 pivotally mounted to the handpiece 204, and a blocking end 266 that fits in the axial space between the end cap 190 and handpiece 204 in the retracted position of FIG. 8A. A linkage bar 268 pivotally attaches midway along the thumb piece 262 and pivotally attaches at its opposite end to the end cap 190.

The retracted position of FIG. 8A corresponds to the retracted position of the balloon catheter 114 in the delivery system 110 as in FIG. 3. In this state, the blocking end 266 fits closely between the facing surfaces of the spaced-apart end cap 190 and handpiece 204, and thus presents a physical barrier to distal advancement of the end cap and balloon catheter within the delivery system 110. At the appropriate moment, the surgeon pivots the toggle lever 260 in the direction of the arrow 270 in FIG. 8B, which simultaneously removes the blocking end 266 from between the end cap 190 and handpiece 204 and pulls the end cap toward the handpiece by virtue of the linkage bar 268. Pivoting the toggle lever 260 the full extent of its travel completely deploys the balloon catheter 114 and displaces the balloon 112 to its proper position within the anchoring skirt 26. That is, the distance traveled by the end cap 190 relative to the handpiece 204 is calibrated to be precisely the same distance necessary to advance the balloon 112 to a location for proper expansion of the anchoring skirt 26 that ensures its optimum hemodynamic performance. Consequently, not only does the toggle lever 260 prevent premature deployment of the balloon catheter, but it also ensures advancement thereof prior to balloon inflation, and in so doing ensures accurate advancement. Additionally, due to the connected nature of the toggle lever 260, there are no loose parts to interfere with the procedure or potentially be misplaced during the surgery. Further details on ensuring the correct positioning of the balloon 112 within the skirt 26 are provided below.

When the surgeon pushes the toggle lever 260 into the advanced position, it desirably snaps into some feature on the handpiece 204 to signal complete deployment and to hold it in place. For instance, FIG. 8C shows a distal tip 272 of the lever 260 captured in a complementary notch or recess in the exterior of the handpiece 204. Of course, numerous other such configurations are possible, and in general the toggle lever 260 and its interaction with the end cap 190 and handpiece 204 are exemplary only. Alternatives such as sliders, rotating knobs or levers, colored or even lighted indicators, etc., are contemplated. The purpose of such alternatives is to prevent premature advancement of the balloon catheter, ensure advancement before balloon inflation, and ensure accurate advancement within the anchoring skirt 26 of the prosthetic heart valve 20.

Other devices to prevent premature balloon catheter deployment/balloon inflation are contemplated, including physical impediments such as the toggle lever 260 described above as well as visual or audible indicators to prevent deployment. For instance, an alternative configuration that impedes balloon inflation fluid flow prior to catheter advancement is seen in FIGS. 9-12, which schematically illustrate systems where a port for fluid used to inflate the balloon on the catheter must be first opened prior to balloon expansion.

FIG. 9 is an elevational view of a portion of the proximal end of an alternative delivery system 110 similar to the views of FIGS. 8A-8C, and showing the relatively movable end cap 190 of the balloon catheter 114 and handpiece 204. A tubular extension 350 of the end cap 190 shown schematically in FIG. 10A includes a closed distal end 352 and a pair of side ports 354 just proximal to the distal end. (It should be noted that the inflation tube 199 previously shown that connects to the distal balloon 112 is omitted to show the fluid flow control.) The tubular extension 350 fits closely within a bore 356 formed in a proximal end of the handpiece 204. Prior to balloon expansion, the components are positioned as seen in FIG. 10B, with the distal end of the tubular extension 350 positioned within the bore 350 such that the side ports 354 are blocked. Distal movement of the end cap 190 as seen in FIG. 10C causes the tubular extension 350 to project from within the bore 356 into a larger chamber 358, thus exposing the side ports 354 so the fluid may be injected toward the distal balloon. In this configuration, the end cap 190 must first move distally relative to the handpiece 204, thus advancing the distal balloon 112, before fluid can be injected to inflate the balloon.

FIG. 11 also shows a portion of the proximal end of an alternative delivery system 110 similar to the views of FIGS. 9-10, with the relatively movable end cap 190 of the balloon catheter 114 and handpiece 204. A tubular extension 360 of the end cap 190 shown exploded in FIG. 12A again includes a distal end closed by a plunger 362 and has a pair of side ports 364 just proximal to the distal end. The tubular extension 350 fits closely within a bore 366 formed in a proximal end of the handpiece 204. Prior to balloon expansion, the components are positioned as seen in FIG. 12B, with the plunger 362 sealed against the opening to the bore 366 such that the side ports 364 are blocked. Distal movement of the end cap 190 as seen in FIG. 12C causes movement of the plunger 362 into a larger chamber 368, thus opening the side ports 364 so the fluid may be injected toward the distal balloon. As with FIGS. 10A-10C above, the balloon inflation tube 199 that connects to the distal balloon 112 is omitted to show the fluid flow control. Again, this configuration ensures that the end cap 190 must first move distally relative to the handpiece 204, thus displacing the balloon 112, before fluid can be injected to inflate the balloon.

Figure 13:
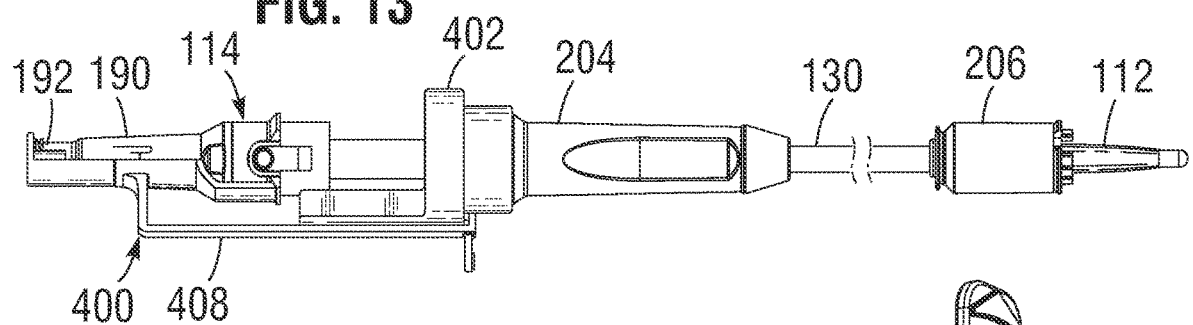
FIG. 13 is a side elevational view of an exemplary heart valve delivery system having a safety clip attached on a proximal end that prevents premature inflation of a dilatation balloon.

FIG. 13 shows the heart valve delivery system 110 described herein having an alternative safety guard 400 attached on a proximal end thereof. As will be explained, the safety guard 400 prevents premature inflation of the dilatation balloon 112 of the balloon catheter 114.

Figure 14A:
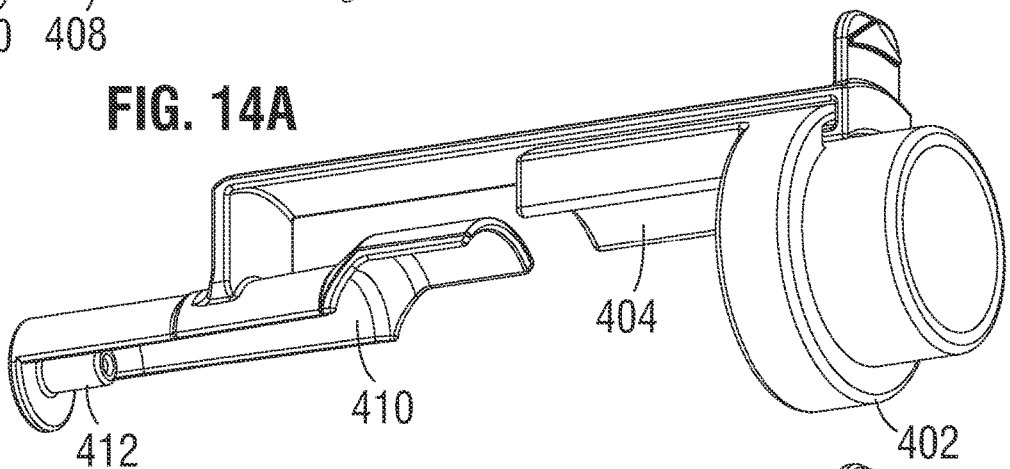
FIGS. 14A-14C are perspective views of the safety clip of FIG. 13 in several deployment positions.
Figure 14B:
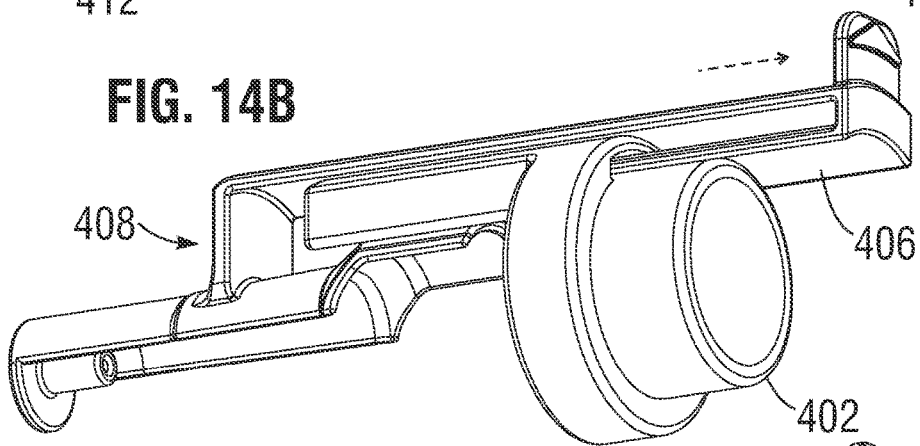
Figure 14C:
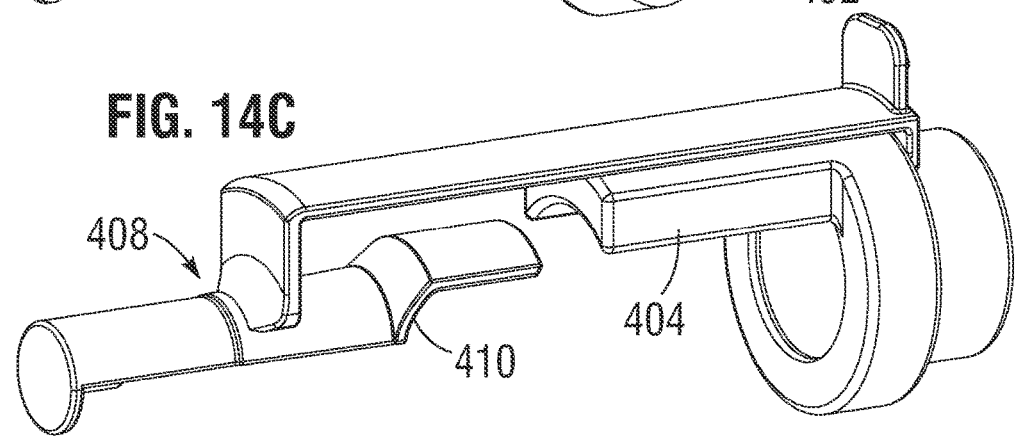

FIGS. 14A-14C illustrate the safety guard 400 of FIG. 13 in several deployment positions. The safety guard 400 includes a distal hub 402 that clips in a fixed position to a proximal end of the handpiece 204 of the delivery system 110. The hub 402 is generally cylindrical and has a proximally-extending guide 404 on one circumferential side thereof. The guide 404 defines an axial channel (not numbered) therein that receives a proximally-directed finger 406 formed on a catheter push member 408. The catheter push member 408 slides axially relative to the distal hub 402 guided by the finger 406 within the channel.

The catheter push member 408 has a catheter engagement piece 410 shaped to conform to the contours of the end cap 190 of the balloon catheter 114, as seen in FIG. 13. The catheter engagement piece 410 further includes an inwardly-directed node 412 that fits closely within the lumen of the luer connector 192, as best seen in FIG. 16A, and provides a physical barrier and visual indicator to prevent premature attachment of a balloon inflation source. It is important to fully advance the balloon catheter 114 prior to inflation of the balloon 112 so as to avoid incorrect expansion of the heart valve, which may cause performance issues and even force valve removal.

FIGS. 15A-15C illustrate a sequence of operation of the heart valve delivery system 110 having the safety guard 400, while FIGS. 16A-16C show the same sequence in longitudinal cross-section. Initially, the safety guard 400 and balloon catheter 114 are in a proximal position with the finger 406 of the push member 408 received completely within the channel formed in the guide 404 of the hub 402 (see FIG. 16A). In this position the balloon 112 of the balloon catheter 114 is retracted within the heart valve (not shown) to facilitate advancement thereof to the implantation site. Once the heart valve has been seated at the annulus, the surgeon advances the balloon catheter 114 by, for example, pushing on the proximal facing surfaces of the push member 408. Ultimately, the end cap 190 engages the handpiece 204 of the introducer, as seen in FIGS. 15B and 16B, signifying full advancement of the balloon 112 within the heart valve. At this position, the finger 406 of the push member 408 emerges from within the channel of the guide 404.

Finally, in FIGS. 15C and 16C, the push member 408 may be detached from the fixed hub 402 and discarded. This exposes the luer connector 192 such that a complementary connector 414 of a fluid inflation system can be attached thereto. The push member 408 cannot be removed until it has been advanced in the distal direction along with the balloon catheter 114 to disengage the finger 406 from within the channel guide 404. This ensures that the connector 414 of a fluid inflation system cannot be coupled to the luer connector 192 until the balloon catheter 114 has been fully advanced, thus ensuring that the balloon 112 is properly positioned within the heart valve prior to inflation.

FIGS. 17A and 17B are perspective views of a still further safety guard 500 of the present application having a toggle lever 502, while FIGS. 18A-18E show the guard on the proximal end of a heart valve delivery system 110 during a sequence of operation. The guard 500 includes a proximal tubular piece 504 having a closed end which fits over and covers the end cap 190 and luer connector 192 of the balloon catheter 114 (see FIG. 18D). As seen in FIGS. 17B and 18B, the tubular piece 502 includes an outwardly-directed circular flange 506 in its midsection, and a plurality of shaped and cantilevered fingers 508 distributed circumferentially around its distal end. The tubular piece 504 fits over the proximal end of the balloon catheter 114 such that the fingers 508 spread apart and snap onto an outwardly-directed rib on the balloon displacer 198, as seen in the enlargement of FIG. 19A.

The toggle lever 502 pivots in an axial plane about hinge points 510 provided on either side of the tubular piece 504, as indicated by the movement arrow in FIG. 18B. The toggle lever extends from flanges 512 that pivot at the hinge points 510 to a thumb tab 514. The distance between the hinge points 510 and the thumb tab 514 is calibrated such that when abutted against the balloon catheter 114, the thumb tab 514 provides a barrier to distal movement of the catheter. That is, the thumb tab 514 abuts against the proximal face of the handpiece 204.

FIGS. 19A and 19B are enlarged sectional views through a portion of the safety guard 500 and heart valve delivery system 110 illustrating relative engagement and disengagement thereof. More particularly, when the balloon catheter 114 is in the retracted position of FIG. 18A, as held by the toggle lever 502, each of the cantilevered fingers 508 engages the outward circular rib on the balloon displacer 198, as seen in FIG. 19A. By pivoting the toggle lever 502 upward, the user may advance the balloon catheter 114 distally relative to the handpiece 204, as seen in FIGS. 18B and 18C. The outwardly-directed circular flange 506 provides a convenient pushing surface. Eventually, a distal end of the balloon displacer 198 fits within the tubular end of the handpiece 204, which causes the proximal edge of the handpiece to cam an angled surface of the cantilevered fingers 508 outward, as seen in FIG. 19B. At this point there is nothing preventing the user from pulling the safety guard 500 off of the end cap 190, thus exposing the luer connector 192, as seen in FIG. 18D. Ultimately, a mating luer connector 516 at the end of a fluid delivery tube 518 can be attached to the luer connector 192, thus providing fluid to the balloon catheter 140.

The safety guard 500 thus provides two important safety functions. First, by imposition of the toggle lever 502 between the balloon catheter 114 and the handpiece 204, the user cannot advance the balloon catheter relative to the remainder of the delivery system 110. Thus, while the user advances the heart valve on the distal end of the delivery system 110 to the implantation site, he/she cannot inadvertently advance the dilatation balloon 112 through the heart valve. Once the heart valve is seated at the annulus, the user flips the toggle lever 502 outward, thus enabling advancement of the balloon catheter 114. At the full extent of the balloon catheter travel, the cantilevered fingers 508 are released by engagement with the handpiece 204, and the safety guard 500 can be removed, as in FIG. 18D. This allows connection of the fluid supply to the luer connector 192. Thus, the user cannot inflate the balloon 112 prior to its full advancement within the heart valve.

Figure 20A:
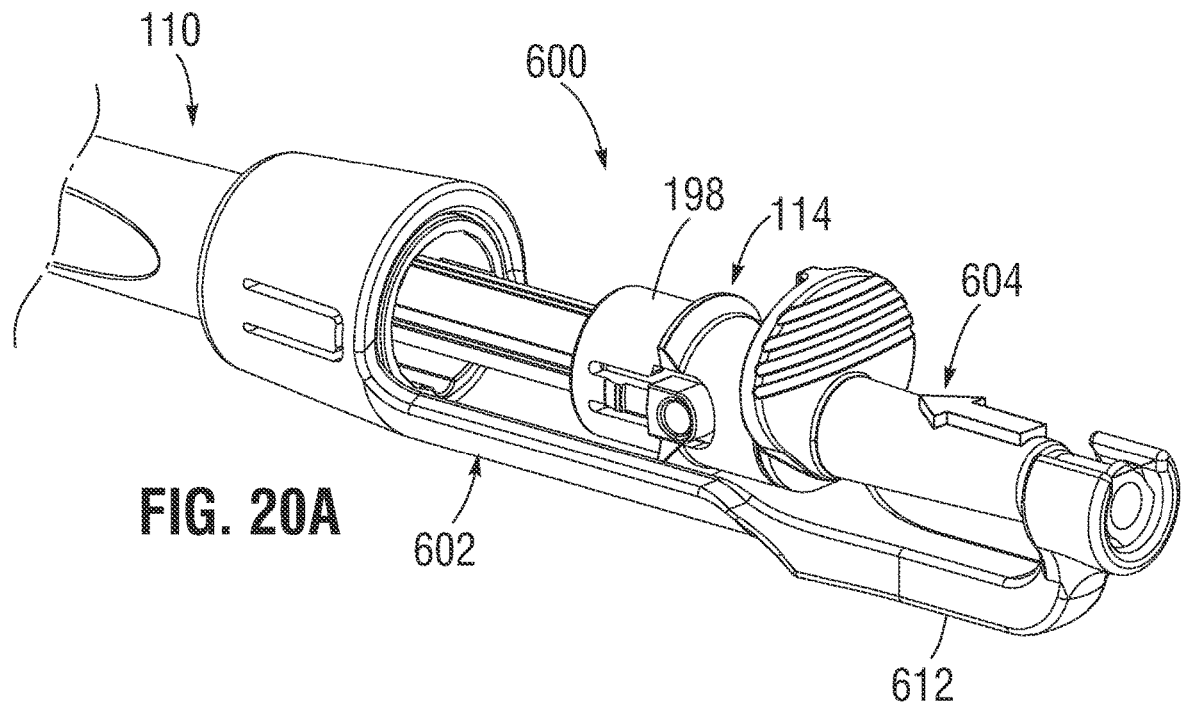
FIGS. 20A and 20B are perspective views of a still further safety guard of the present application showing interaction with a heart valve delivery system with a balloon catheter in both retracted and advanced positions.
Figure 20B:
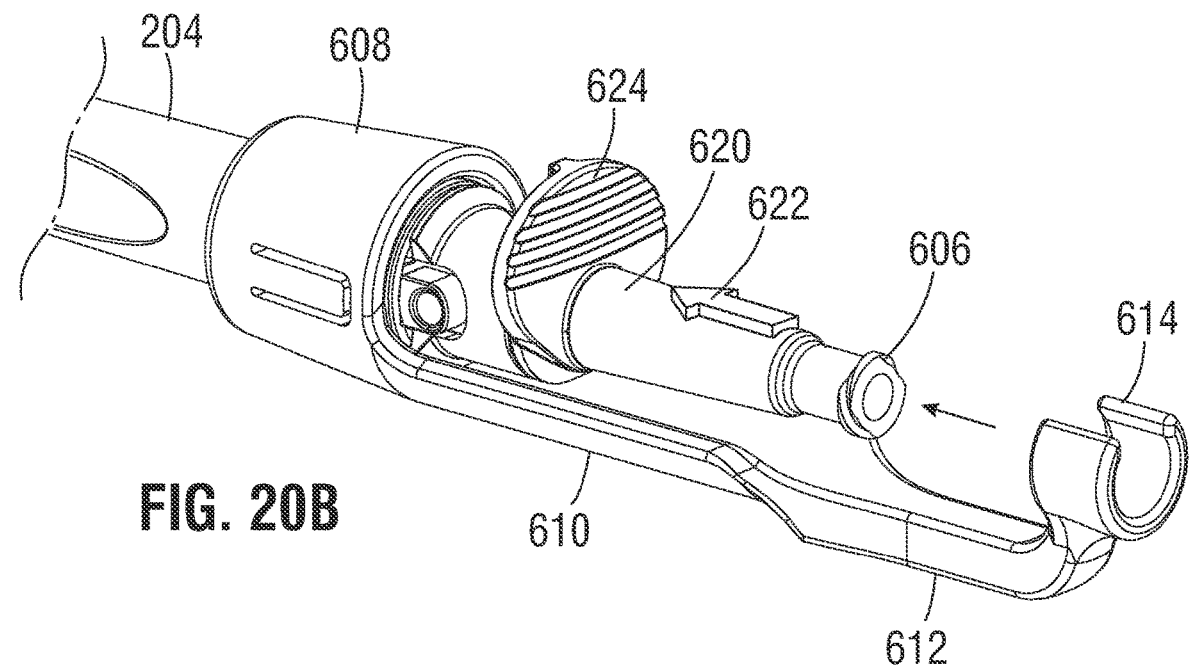

FIGS. 20-21 illustrate a still further safety guard 600 of the present application showing interaction with the proximal end of a heart valve delivery system 110 having a balloon catheter 114, as described above. The safety guard 600 includes a stationary part 602 attached to a proximal end of the handpiece 204, and a movable part 604 connected on a proximal end of the balloon catheter 114 and providing a luer connector 606. That is, the movable part 604 essentially takes the place of the previously-described end cap 190 and luer connector 192, such as shown in FIG. 3, and attaches to the balloon displacer 198.

The stationary part 602 includes a tubular frustoconical sleeve 608 that engages the proximal end of the handpiece 204 in an interference fit, or it may be adhered thereto. An elongated arm 610 extends proximally and generally axially from the sleeve 608 to the proximal end of the movable part 604. The arm 610 parallels closely the balloon catheter 114, but diverges away along an offset section 612 adjacent the movable part 604, at least in the retracted position of the catheter as seen in FIG. 20A. At its proximal end, the arm 610 bends back toward the movable part 604 and provides a partial tubular luer guard 614 centered along the axis of the balloon catheter 114 that receives the luer connector 606. The luer connector 606 is located on the end of a tubular section 620 having an embossed or printed arrow 622 thereon. Just proximal to the balloon displacer 198, an enlarged thumb plate 624 having anti-slip grooves facilitates advancement of the balloon catheter 114 in a one-handed operation.

FIGS. 21A-21E show several steps in the operation of the safety guard 600 during advancement of the balloon catheter 114. Initially, as explained above, the balloon catheter 114 and movable part 604 of the safety guard 600 are retracted such that the luer connector 606 resides within the luer guard 614. In this configuration, a fluid supply system cannot be connected to the balloon catheter 114. After preparing the heart valve and delivery system 110, and advancing the heart valve into position within the target annulus, the user advances the balloon catheter 114 by moving the thumb plate 624 in the direction of the arrow 622 on the tubular section 620. Once the balloon catheter 114 has been fully advanced, the luer connector 606 is exposed in the space created by the offset section 612 of the elongated arm 610, as seen in FIG. 21B. At this point, a mating luer connector 630 on the end of a fluid supply tube 632 can be attached to the luer connector 606 of the balloon catheter 614. Additionally, the fluid supply tube 632 can be captured within the partial tubular luer guard 614 to help prevent stress at the junction of the tube and the mating luer connector 630.

Furthermore, various ways can be provided to prevent premature advancement of the balloon 114 relative to the handpiece 204. For example, a removable safety clip such as the clip 240 described above with respect to FIG. 6 can be provided. Alternatively, to eliminate loose parts, the stationary and movable parts 602, 604 can be provided with cooperating features to prevent their premature relative movement, and to prevent direct axial balloon catheter advancement until the cooperating structures are disengaged.

For instance, the enlarged views of FIGS. 21D and 21E show one version of cooperating features. More particularly, one side of the thumb plate 624 may project outward into interference with a corner 640 of the stationary part 602 at the beginning of the offset section 612. In this way, distal axial movement of the thumb plate 624, and attached balloon catheter 114, is prevented. When advancement of the balloon catheter 114 is desired, the thumb plate 624 may be displaced laterally a short distance, thus freeing it to move distally so as to advance the balloon catheter 114, as seen by the arrows in FIG. 21E. Other configurations are possible, such as providing a movable trigger or latch on either the stationary or movable parts 602, 604.

Figure 22A:
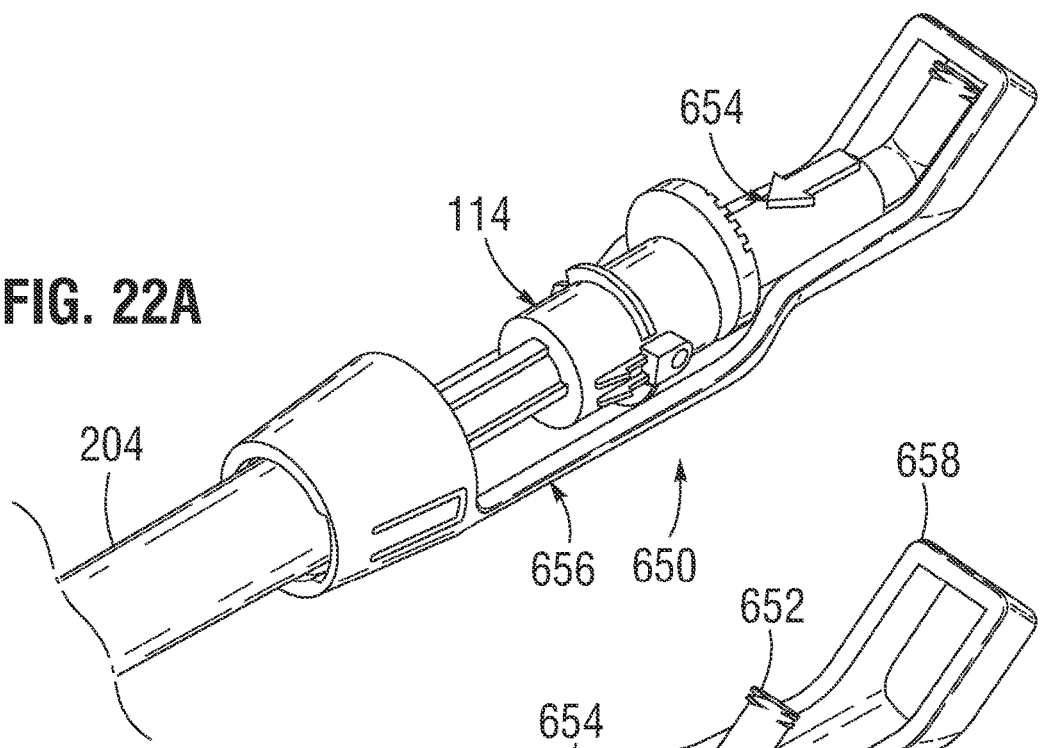
FIGS. 22A-22C are perspective and side elevational views of an alternative safety guard similar to that shown in FIG. 20A and having an angled luer connector.
Figure 22B:
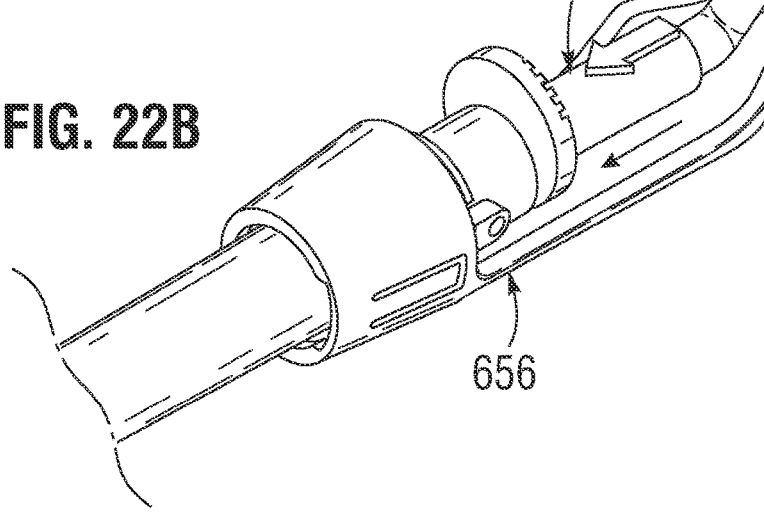
Figure 22C:
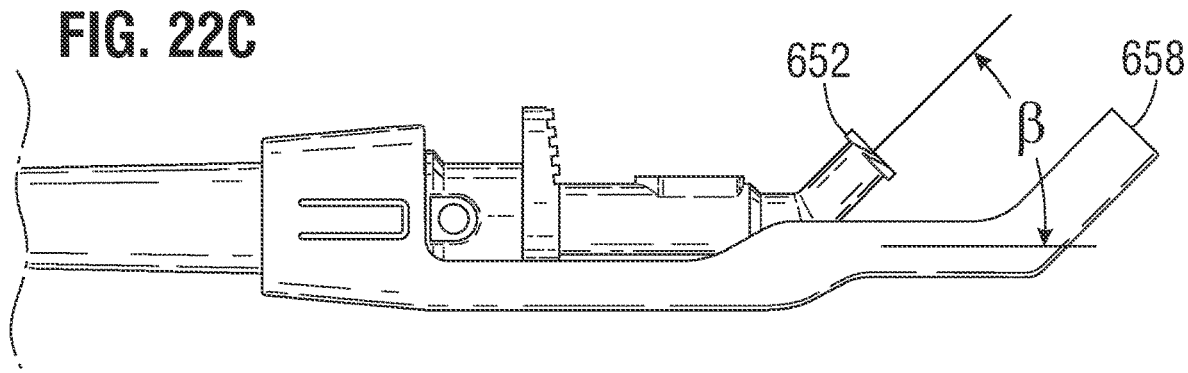

FIGS. 22A-22C illustrate an alternative safety guard 650 similar to that shown in FIG. 20A but having an angled luer connector 652 on a movable part 654. As seen in FIG. 22C, the luer connector 652 extends away from the axis of the balloon catheter at an angle β, preferably between 30-60°, and more preferably about 45°. Additionally, a stationary part 656 attached to the handpiece 204 includes a luer guard 658 having an angle that mimics the angle of the luer connector 652. In the retracted position of FIG. 22A, the luer guard 658 closely receives the luer connector 652 and prevents attachment of a fluid supply thereto. It is only after distal displacement of the balloon catheter 114 and the attached movable part 654 can a fluid supply luer connector be attached to the luer connector 652. Additionally, means for preventing premature advancement of the balloon 114 is desirably included, such as a removable safety clip as in FIG. 6, or cooperating features between the movable part 654 and stationary part 656, such as seen in FIGS. 21D and 21E.

Figure 23A:
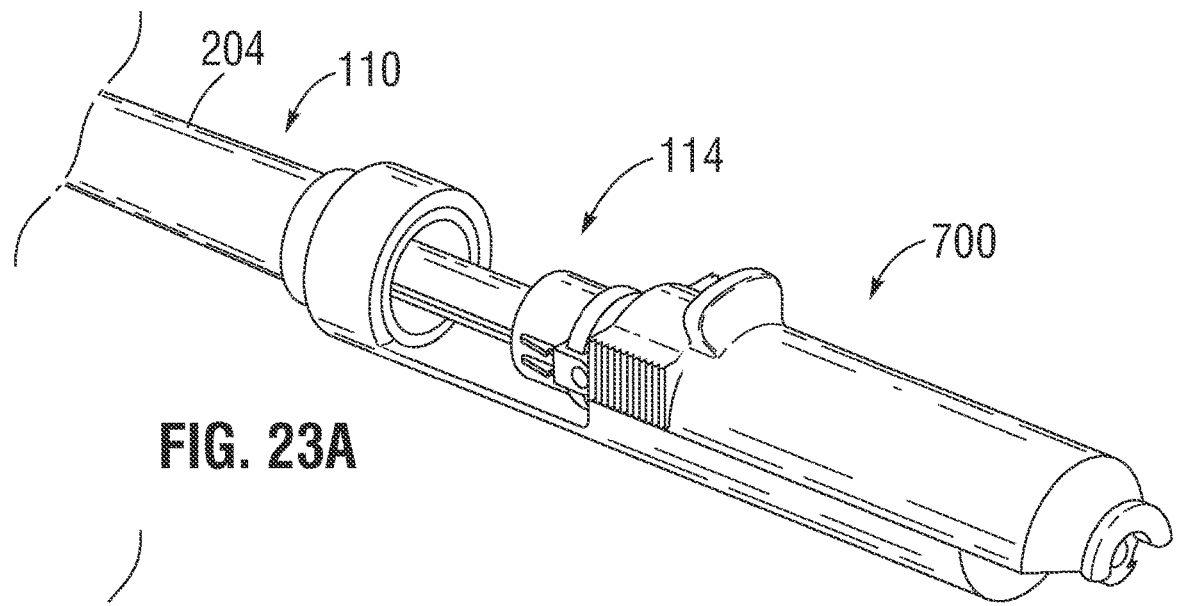
FIGS. 23A-23C are perspective and longitudinal sectional views through a still further alternative safety guard of the present application.
Figure 23B:
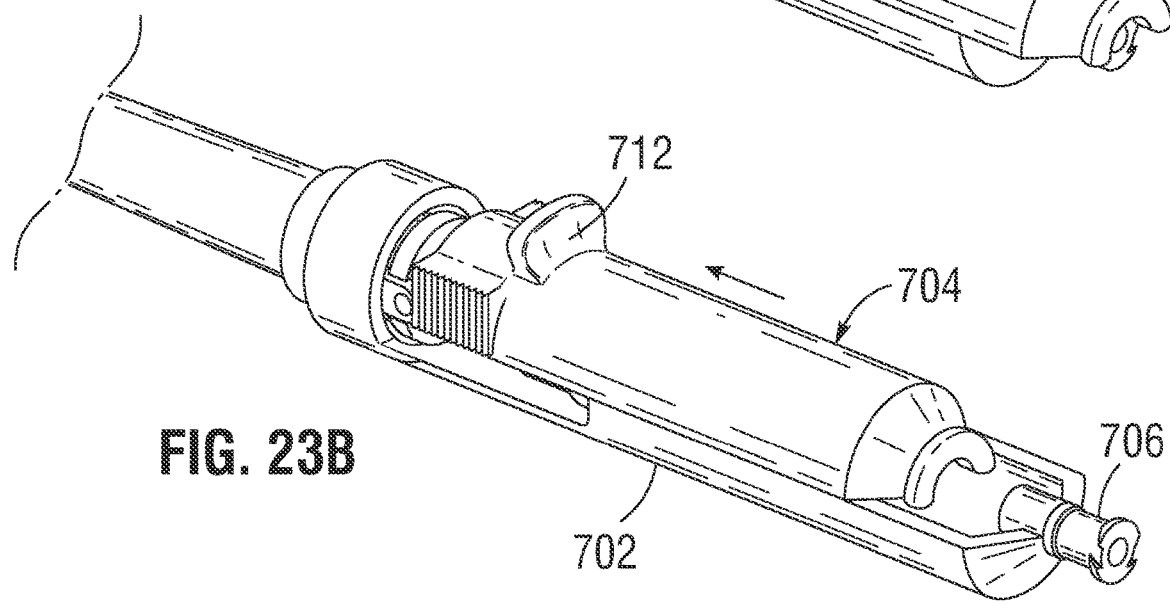
Figure 23C:
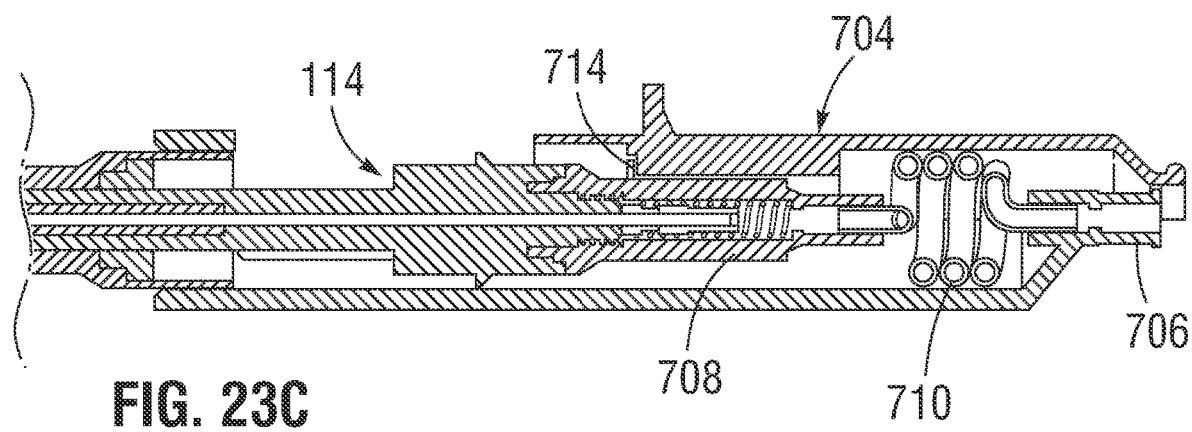

In FIGS. 23A-23C, another safety guard 700 of the present application is shown having a semi-tubular stationary part 702 connected to the handpiece 204 of the heart valve delivery system 110, and a semi-tubular movable cover 704 that slides axially over the stationary part. As seen in the sectional view of FIG. 23C, the stationary part 702 includes a luer connector 706 on its proximal end. An end cap 708 of the balloon catheter 114 fluidly connects to the luer connector 706 via a coiled flexible tube 710 positioned in the cylindrical space between the stationary and movable parts 702, 704. In this way, the balloon catheter 114 can slide axially relative to the stationary part 702 while remaining in fluid communication with the proximal luer connector 706. However, in its retracted position shown in FIG. 23A, the movable cover 704 extends over the luer connector 706 and prevents attachment of a fluid supply thereto. This prevents premature inflation of the balloon of the balloon catheter 114 prior to advancement thereof through the heart valve. The movable cover 704 includes a thumb tab 712 which a user can press to axially move the cover in a one-handed operation. An inner shoulder 714 of the movable cover 704 engages a portion of the balloon catheter 114 and pushes it distally. As before, a solution for preventing premature advancement of the balloon 114 is desirably included, such as a removable clip as in FIG. 6, or cooperating features between the movable cover 704 and stationary part 702 such as in FIGS. 22D and 22E.

It should be understood that individual features of the various safety guards and clips described herein can be interchanged. For instance, as mentioned above, the removable safety clip 240 of FIG. 6 can be supplied with the safety guards disclosed in FIGS. 20-23. Likewise, the cooperating features between the movable and stationary parts as shown in FIGS. 22D and 22E can be incorporated into the earlier-described safety guards. In short, any conceivable combination of the individual features of the safety clips and safety guards disclosed herein can be made and should be considered part of the present application.

Various heart valves may be utilized in combination with the delivery system components described herein, and any combination not otherwise explicitly described is contemplated. Indeed, FIGS. 24A-24C illustrate the delivery system 110 used to deploy a fully expandable heart valve, such as is typically implanted percutaneously. The delivery system 110 may be advanced into implant position using a traditional open heart surgical technique, or with a less-invasive approach, such as through a mini-thoracotomy. The surgeon positions the fully expandable heart valve in a correct position and alignment within the annulus and expands it using a balloon or other expander. Fully expandable prosthetic heart valves have been developed primarily for use in percutaneous procedures because of the ability to implant the valve without placing the patient on cardiopulmonary bypass. However, the delivery system described herein greatly reduces the time on bypass, and provides a number of other benefits which may be applicable to fully expandable valves. Therefore, it should be understood that the delivery systems herein are not limited to so-called "hybrid" valves which have a non-collapsible/non-expandable portion and an expandable stent, but also could be used to implant fully expandable valves.

FIGS. 24A-24C show the distal end of a heart valve delivery system 110, such as those described herein, delivering an expandable/collapsible prosthetic heart valve 800 to a treatment site using a valve holder 802. A similar valve holder 802 is shown in U.S. Patent Publication No. 2009/0281619, filed Oct. 8, 2008, the disclosure of which is expressly incorporated herein.

For the purpose of consistency, like elements of the heart valve delivery system 110 will be given the same numbers as used above. More particularly, the distal end of the delivery system includes a malleable shaft 130 on which is mounted an adapter 208. The adapter 208 receives in its bore a proximal tubular extension 804 from the valve holder 802. As with the earlier-described engagement between the valve holder 22 and valve holder adapter 208, as seen in FIG. 5A, the tubular extension 804 desirably has a circular groove (not numbered) therein that receives an inwardly projecting bump 218 on the adapter 208. A locking sleeve 206 fits closely around the adapter 208 and holds the bump 218 within the groove, thus locking the valve holder 802 onto the distal end of the delivery system 110 and enabling quick release thereof.

The valve holder 802 was a relatively thin distal sleeve portion 806 that is desirably formed of Nitinol, stainless steel, or a polymer such as nylon, PET, PEEK, PE, Pebax, Urethane, and PVC. Prosthetic heart valve 800 is initially crimped onto the distal end portion of the sleeve 806. Desirably, sleeve 806 is formed as a braid or with laser cuts, so that it can expand radially during implantation of the valve 800 at the treatment site. If desired, the sleeve 806 can be formed with only a portion of it braided or laser cut where the valve 800 is crimped thereon, so that the braided portion of the sleeve 806 can be expanded along with valve 800.

Various expandable heart valves are known in the art, and the present application should not be considered limited to any particular one. Such valves typically include a tubular stent frame 810 within which a plurality of flexible leaflets or a xenograft valve (not shown) are attached to provide blood occluding surfaces. The stent frame 810 may be similar to an expandable Stainless Steel stent used in the SAPIEN Transcatheter Heart Valve available from Edwards Lifesciences of the Irvine, Calif.

After the valve 800 is in position for deployment, the surgeon urges the balloon 112 distally relative to malleable shaft 130 and positions it within the valve 800, as shown in FIG. 24B. FIG. 24C shows the balloon 112 in an expanded state to expand both the sleeve 806 and the valve 800 against the annulus. Once valve 800 is expanded to the desired diameter, the balloon 112 can be deflated (not shown) and the delivery system 110 retracted from the patient's vasculature. Preferably, sleeve 806 is formed of a resilient material that enables it to spring back inward and be removed along with the delivery system 110.

While the invention has been described in its preferred embodiments, it is to be understood that the words which have been used are words of description and not of limitation. Therefore, changes may be made within the appended claims without departing from the true scope of the invention.

What is claimed is:

1. A method of delivery and implant of a prosthetic heart valve at a valve annulus, comprising:
   providing a delivery system including:
      a shaft having a lumen therethrough; and
      a balloon catheter extending through the shaft having a balloon on a distal end and a proximal luer connector, the balloon catheter being capable of linear movement relative to the shaft from a retracted position to an advanced position;

providing a heart valve including a prosthetic valve having an expandable frame, the expandable frame having a contracted state for delivery to an implant position and an expanded state configured for outward connection to the annulus, the heart valve being mounted on a distal end of the shaft;

advancing the distal end of the shaft so that the heart valve with the expandable frame in its contracted state is located at the implant position adjacent the annulus;

ensuring that the balloon cannot expand until the balloon catheter is displaced distally to the advanced position by covering the luer connector with a safety member;

displacing the balloon catheter distally to the advanced position and the balloon is located within the expandable frame of the heart valve;

removing the safety member from covering the luer connector; and inflating the balloon within the expandable frame.

2. The method of claim 1, wherein step of displacing cannot occur until removal of the safety member from covering the luer connector.

3. The method of claim 1, wherein the step of inflating converts the expandable frame from its contracted state to its expanded state.

4. The method of claim 1, wherein the step of displacing occurs simultaneously with the step of removing.

5. The method of claim 4, wherein the safety member comprises a luer guard fixed with respect to the shaft and surrounding the luer connector, and displacing the balloon catheter distally to the advanced position moves the luer connector from within the luer guard to enable coupling of a mating connector of a fluid source to the luer connector.

6. The method of claim 5, wherein the delivery system has a handpiece fixed to a proximal end of the shaft, and further including a thumb plate connected to displace the balloon catheter relative to the handpiece, the step of displacing comprising pushing the thumb plate.

7. The method of claim 1, wherein the delivery system has a handpiece fixed to a proximal end of the shaft, and further including cooperating structures on the handpiece and balloon catheter that prevents axial balloon catheter advancement until the cooperating structures are disengaged.

8. The method of claim 1, wherein the heart valve is fully expandable and mounts onto a flexible tubular valve holder connected to the distal end of the shaft, and inflation of the balloon expands the valve holder and the heart valve mounted thereon.

9. The method of claim 1, wherein a proximal end of the balloon catheter projects proximally from out of the shaft, and the safety member engages in a first position between a portion of the balloon catheter that projects from the shaft and a proximal end of the shaft to prevent distal movement of the balloon catheter relative to the shaft, and the balloon cannot expand until the safety member is displaced from the first position.

10. The method of claim 9, wherein in the first position the safety member covers the luer connector on the balloon catheter and ensures that the balloon cannot expand.

11. A method of delivery and implant of a prosthetic heart valve at a valve annulus, comprising:
providing a delivery system including:
a shaft having a lumen therethrough;
a balloon catheter extending through the shaft having a balloon on a distal end and a proximal luer connector; and
a safety member arranged in a first position on the shaft covering the luer connector so as to prevent premature expansion of the balloon, the safety member being displaceable to a second position away from the luer connector to permit expansion of the balloon;

providing a heart valve including a prosthetic valve having an expandable frame, the expandable frame having a contracted state for delivery to an implant position and an expanded state configured for outward connection to the annulus, the heart valve being mounted on a distal end of the shaft;

advancing the distal end of the shaft so that the heart valve with the expandable frame in its contracted state is located at the implant position adjacent the annulus;

ensuring that the balloon cannot expand until the safety member is displaced away from the first position;

displacing the safety member from the first position to the second position; and inflating the balloon within the expandable frame.

12. The method of claim 11, wherein step of displacing cannot occur until removal of the safety member from covering the luer connector.

13. The method of claim 11, wherein the step of displacing occurs simultaneously with the step of removing.

14. The method of claim 13, wherein the safety member comprises a luer guard fixed with respect to the shaft and surrounding the luer connector, and displacing the balloon catheter distally to the advanced position moves the luer connector from within the luer guard to enable coupling of a mating connector of a fluid source to the luer connector.

15. The method of claim 14, wherein the delivery system has a handpiece fixed to a proximal end of the shaft, and further including a thumb plate connected to displace the balloon catheter relative to the handpiece, the step of displacing comprising pushing the thumb plate.

16. The method of claim 11, wherein the step of inflating converts the expandable frame from its contracted state to its expanded state.

17. The method of claim 11, wherein the heart valve is fully expandable and mounts onto a flexible tubular valve holder connected to the distal end of the shaft, and inflation of the balloon expands the valve holder and the heart valve mounted thereon.

18. The method of claim 11, wherein a proximal end of the balloon catheter projects proximally from out of the shaft, and the safety member engages between a portion of the balloon catheter that projects from the shaft and a proximal end of the shaft.

19. The method of claim 18, wherein the balloon catheter is capable of linear movement relative to the shaft from a retracted position to an advanced position, and when in the first position the safety member prevents distal movement of the balloon catheter relative to the shaft.

20. The method of claim 11, wherein the safety member comprises a locking clip that snaps onto a handpiece at the proximal end of the shaft and onto a proximal end of the balloon catheter, the locking clip preventing expansion of the balloon.

* * * * *